United States Patent
Takai

(10) Patent No.: US 9,505,005 B2
(45) Date of Patent: Nov. 29, 2016

(54) TUBE SORTER, SAMPLE PROCESSING SYSTEM, AND SAMPLE TRANSPORTING METHOD

(71) Applicant: Sysmex Corporation, Kobe-shi, Hyogo (JP)

(72) Inventor: Kei Takai, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 13/953,334

(22) Filed: Jul. 29, 2013

(65) Prior Publication Data

US 2014/0037517 A1    Feb. 6, 2014

(30) Foreign Application Priority Data

Jul. 31, 2012 (JP) .................................. 2012-169397

(51) Int. Cl.
| | |
|---|---|
| B01L 9/06 | (2006.01) |
| B65G 65/00 | (2006.01) |
| G01N 35/02 | (2006.01) |
| G01N 35/04 | (2006.01) |

(52) U.S. Cl.
CPC ............... B01L 9/06 (2013.01); B65G 65/00 (2013.01); G01N 35/02 (2013.01); *G01N 2035/0465* (2013.01)

(58) Field of Classification Search
CPC ............ G01N 2035/0465; G01N 35/02; B65G 65/00; B01L 9/06
See application file for complete search history.

(56) References Cited

U.S. PATENT DOCUMENTS

| | | | |
|---|---|---|---|
| 6,117,392 A * | 9/2000 | Hanawa | G01N 35/00603 422/65 |
| 6,290,907 B1 * | 9/2001 | Takahashi et al. | 422/65 |
| 2002/0028157 A1 * | 3/2002 | Takahashi | G01N 35/026 422/65 |
| 2003/0235514 A1 * | 12/2003 | Nogawa et al. | 422/65 |
| 2008/0069730 A1 * | 3/2008 | Itoh | 422/65 |
| 2009/0162247 A1 * | 6/2009 | Tokieda | G01N 35/026 422/65 |
| 2010/0028124 A1 * | 2/2010 | Lackner et al. | 414/806 |
| 2011/0076193 A1 * | 3/2011 | Kitagawa | G01N 35/026 422/65 |
| 2013/0197690 A1 * | 8/2013 | Suzuki et al. | 700/216 |

FOREIGN PATENT DOCUMENTS

| | | |
|---|---|---|
| JP | 2-85361 | 7/1990 |
| JP | 3-38704 Y2 | 8/1991 |
| JP | 6-34642 | 10/1994 |
| JP | 5142232 A | 5/2000 |
| JP | 2001108690 A | 4/2001 |
| JP | 2002-040034 A | 2/2002 |
| JP | 2003232798 | 8/2003 |
| JP | 2003232798 A * | 8/2003 |
| WO | WO2012043261 A1 * | 5/2012 |

* cited by examiner

*Primary Examiner* — Jill Warden
*Assistant Examiner* — Benjamin Whatley
(74) *Attorney, Agent, or Firm* — Brinks Gilson & Lione

(57) ABSTRACT

A tube sorter includes a rack stocker configured to have stocked therein a sample rack capable of holding one or more sample tubes. A transporting section is configured to transport the sample rack and a tube conveyor is configured to unload a sample tube from the sample rack and load the sample tube onto a sample rack supplied from or stocked in the rack stocker. A rack pushing mechanism is configured to convey an empty sample rack or a sample rack to be emptied to the rack stocker.

21 Claims, 15 Drawing Sheets

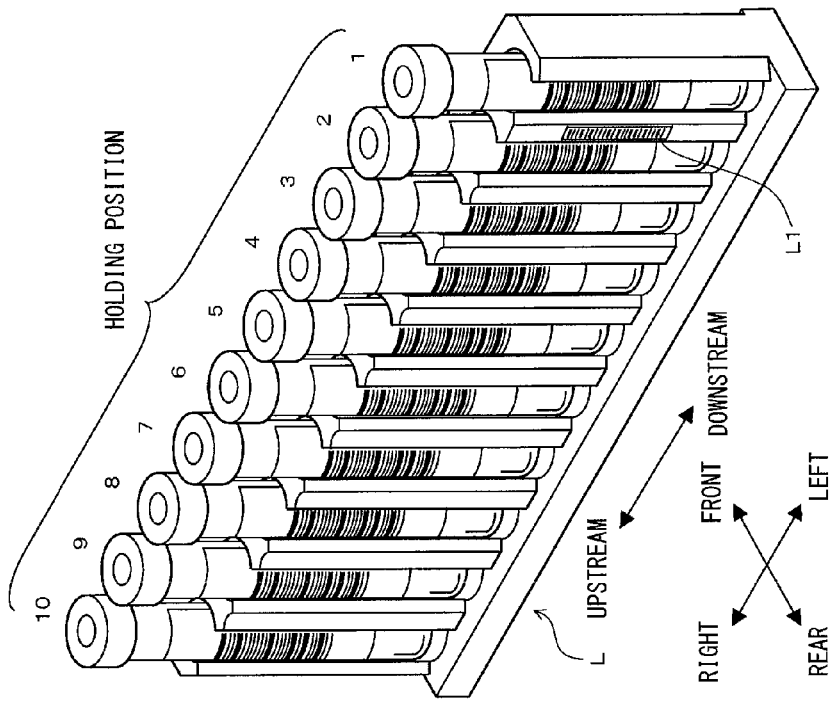
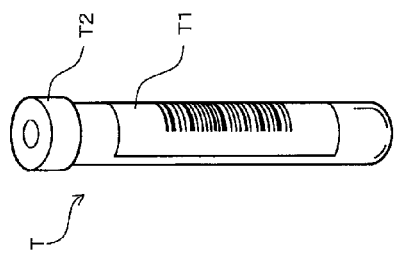
F I G. 2 A
F I G. 2 B

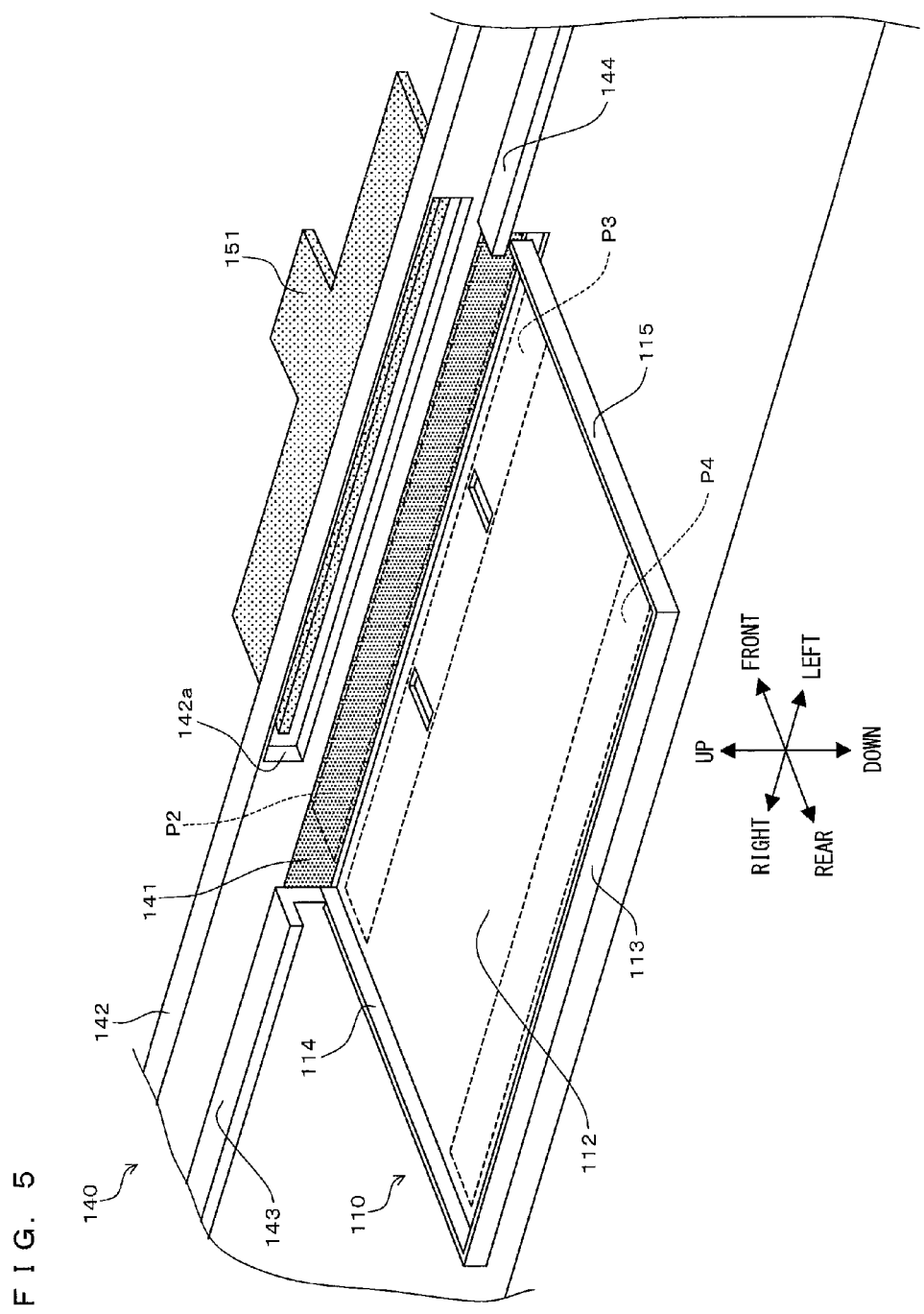

FIG. 10A

| HOLDING POSITION | SAMPLE ID | TRANSFER INFORMATION |
|---|---|---|
| 1 | ID001 | TRANSFER UNNECESSARY |
| 2 | ID002 | TRANSFER UNNECESSARY |
| 3 | ID003 | TRANSFER UNNECESSARY |
| 4 | ID004 | TRANSFER UNNECESSARY |
| 5 | ID005 | TRANSFER UNNECESSARY |
| 6 | ID006 | BUFFER RACK REGION 120a |
| 7 | ID007 | BUFFER RACK REGION 120b |
| 8 | ID008 | SORTING RACK |
| 9 | NG | SORTING RACK |
| 10 | --- | --- |

FIG. 10B

| HOLDING POSITION | SAMPLE ID | TRANSFER INFORMATION |
|---|---|---|
| 1 | ID001 | ARCHIVE RACK |
| 2 | ID002 | ARCHIVE RACK |
| 3 | ID003 | ARCHIVE RACK |
| 4 | ID004 | ARCHIVE RACK |
| 5 | ID005 | ARCHIVE RACK |
| 6 | --- | --- |
| 7 | --- | --- |
| 8 | --- | --- |
| 9 | --- | --- |
| 10 | --- | --- |

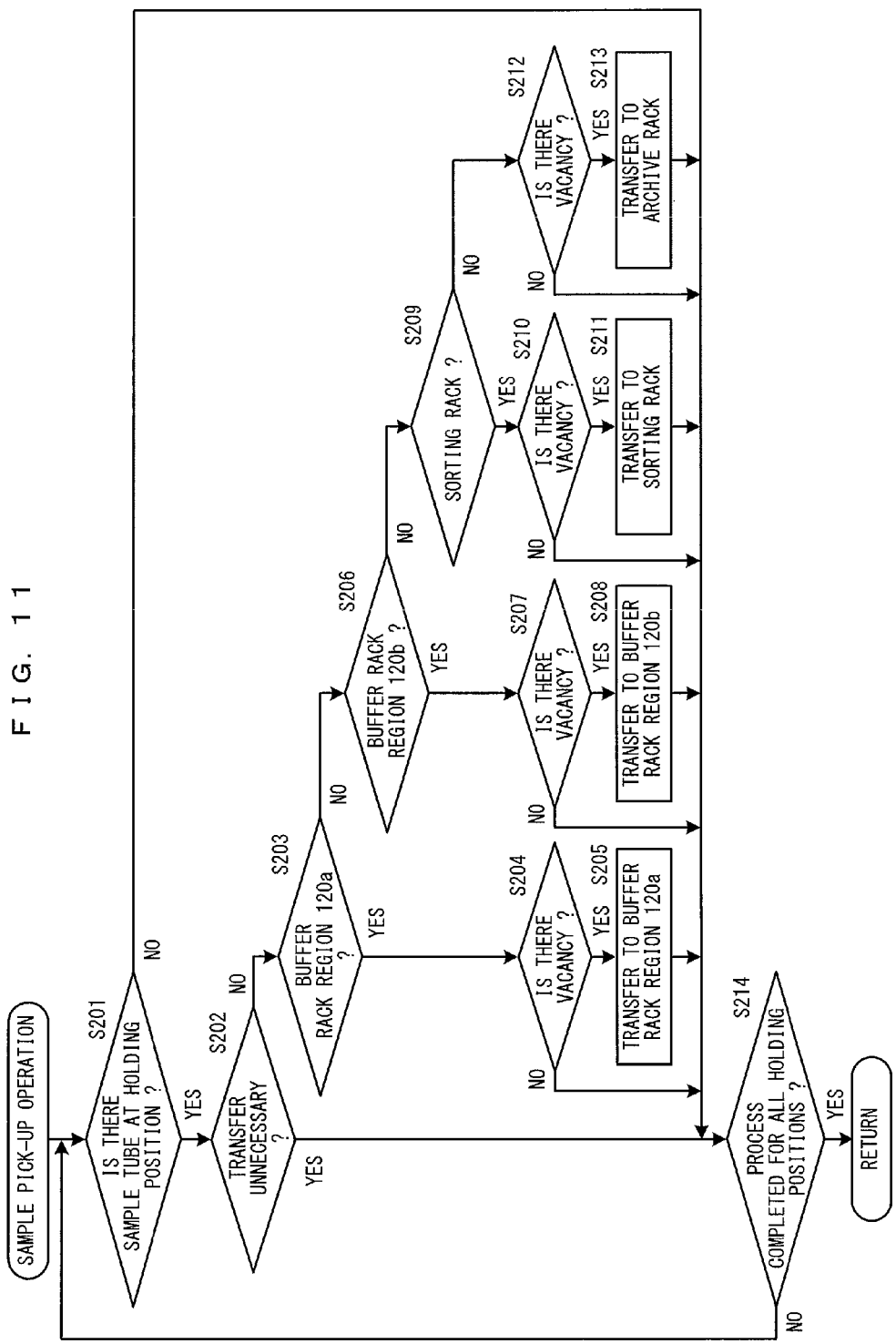
F I G. 1 1

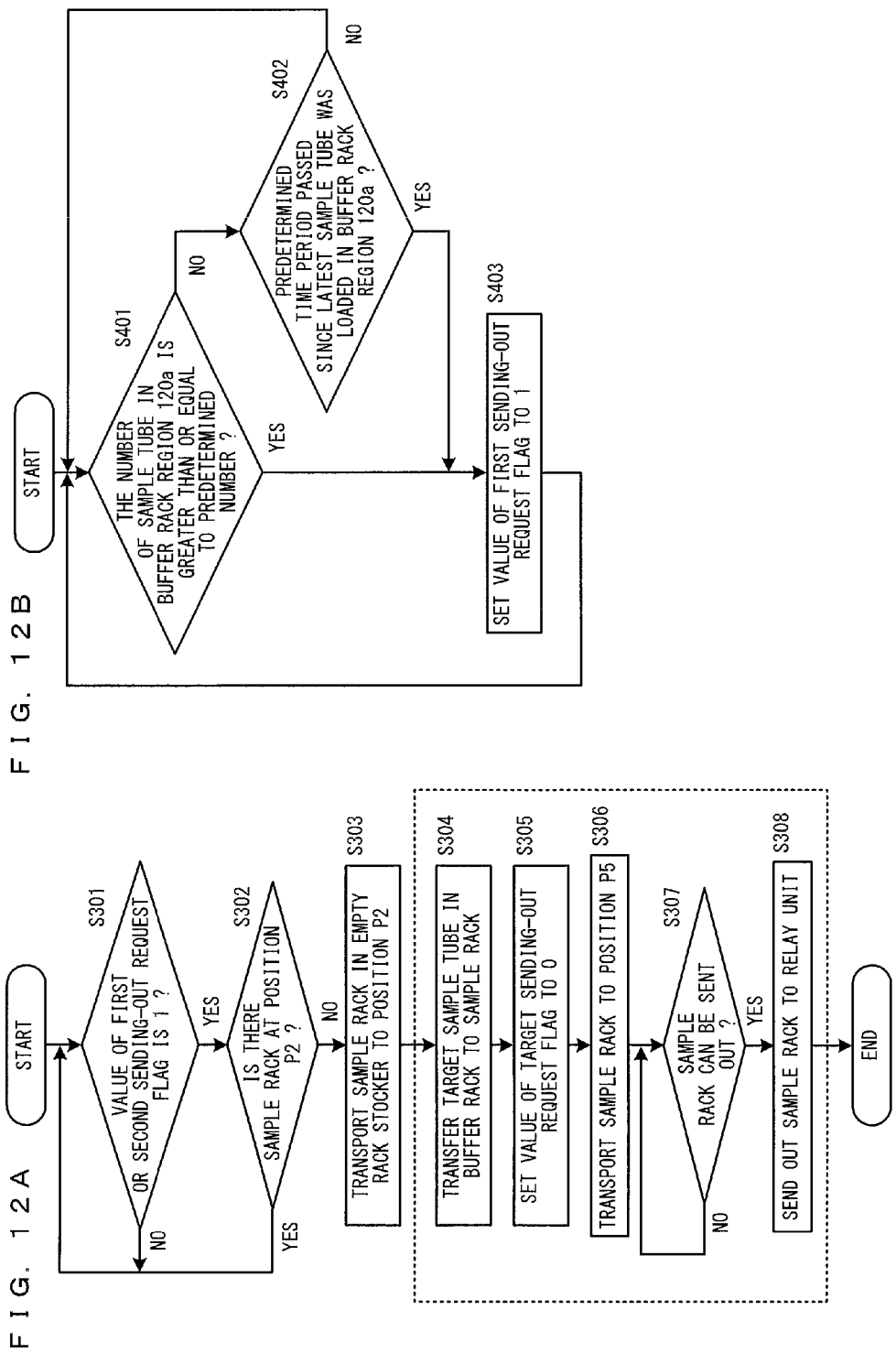

TUBE SORTER, SAMPLE PROCESSING SYSTEM, AND SAMPLE TRANSPORTING METHOD

RELATED APPLICATIONS

This application claims priority under 35 U.S.C. §119 to Japanese Patent Application No. 2012-169397 filed on Jul. 31, 2012, the entire content of which is hereby incorporated by reference.

FIELD OF THE INVENTION

The present invention relates to a tube sorter for transferring a sample tube containing a sample, from a sample rack to another sample rack.

BACKGROUND OF THE INVENTION

To date, there have been known sample sorting apparatuses which automatically sort sample tubes containing samples, in accordance with test types, test items, and the like. See Japanese Laid-Open Patent Publication No. 2002-40034.

JP2002-40034 discloses a sample sorting apparatus which sorts sample tubes in accordance with test types. Here, three rack housing sections are provided corresponding to three test types, and a plurality of empty sample racks are housed in each rack housing section in advance. When a sample rack holding sample tubes is fed to the sample sorting apparatus, a sample tube is taken out of the sample rack and the taken-out sample tube is conveyed to a sample rack in a rack housing section corresponding to its test type. After sample tubes are sorted in this manner, sample racks in the rack housing sections are transported to a testing apparatus.

In the sample sorting apparatus referred, when empty sample racks are not set in the rack housing sections, a user needs to prepare an empty sample rack and set it in a rack housing section. Thus, the greater the number of processes of samples is, the more frequently empty sample racks have to be set, which may impose troublesome work on the user.

SUMMARY OF THE INVENTION

A first aspect of the present invention is a tube sorter comprising: a rack stocker configured to stock therein a sample rack capable of holding one or more sample tubes; a transporting section configured to transport a sample rack; a tube conveyor configured to perform an unloading operation of unloading a sample tube from a sample rack that was transported by the transporting section and a loading operation of loading the sample tube onto a sample rack supplied from or stocked in the rack stocker; and a rack conveyor configured to convey an empty sample rack or a sample rack to be emptied, that was transported by the transporting section, to the rack stocker.

A second aspect of the present invention is a sample processing system comprising: the tube sorter according described above, a sample processing apparatus configured to process a sample in a sample tube, and a transporting apparatus configured to transport a sample rack holding a sample tube sorted by the tube sorter, to the sample processing apparatus.

A third aspect of the present invention is a sample transporting method employing a tube sorter, the rack transporting method comprising: unloading one or more sample tubes held in a sample rack in accordance with a sorting rule; stocking, when the sample rack has become empty by the one or more sample tubes having been unloaded, the sample rack in a rack stocker; and using an empty sample rack in the rack stocker in order to transport the unloaded one or more sample tubes.

BRIEF DESCRIPTION OF THE DRAWINGS

FIG. 2A shows a structure of a sample tube according to an embodiment.

FIG. 2B shows a structure of a sample rack according to an embodiment.

FIG. 5 is a perspective view showing a vicinity of a part where an empty rack stocker is connected to a transport path according to an embodiment.

FIG. 10A shows a concept of an example of obtained transfer information according to an embodiment.

FIG. 10B shows a concept of an example of obtained transfer information according to an embodiment.

FIG. 11 is a flow chart showing a sample pick-up operation according to an embodiment.

FIG. 12A is a flow chart showing a transport process for a sample rack stocked in the empty rack stocker according to an embodiment.

FIG. 12B is a flow chart showing a process for updating a value of a sending-out request flag according to an embodiment.

DETAILED DESCRIPTION OF THE PREFERRED EMBODIMENTS

The present embodiment is obtained by applying the present invention to a sample processing system for performing tests and analyses of whole blood sample. Hereinafter, the present embodiment will be described with reference to the drawings.

Figure 1:
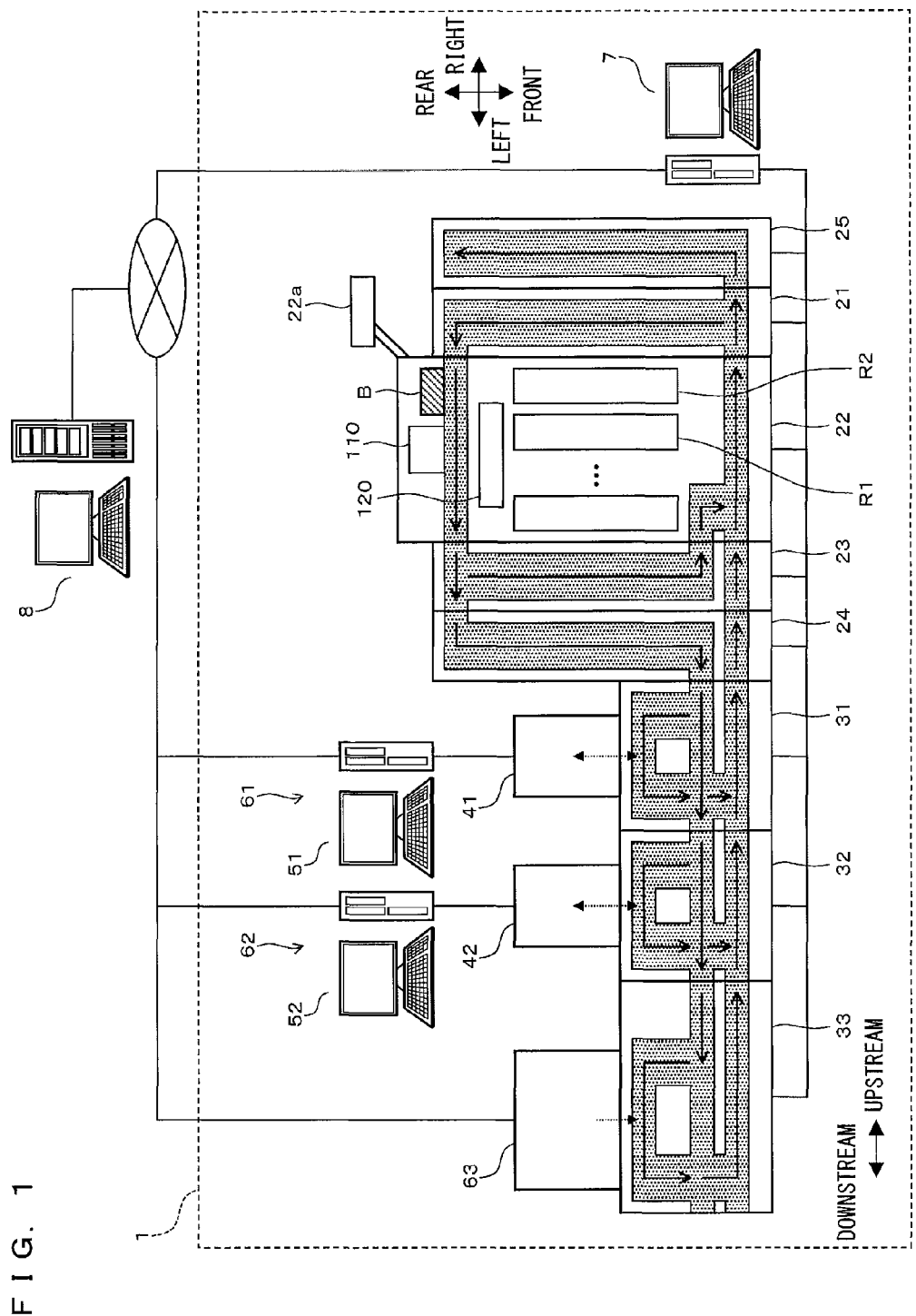
FIG. 1 shows a structure of a sample processing system according to an embodiment, viewed from above.

FIG. 1 shows a structure of a sample processing system 1, viewed from above.

The sample processing system 1 according to the present embodiment includes a feeding unit 21, a tube sorter 22, a relay unit 23, a relay unit 24, a collection unit 25, transporting units 31 to 33, blood cell analyzers 61 and 62, a smear preparing apparatus 63, and a transport controller 7. The blood cell analyzer 61 includes an information processing unit 51, a measurement unit 41, and a sample supplying section 31b (see FIG. 7) being a part of the transporting unit 31. The blood cell analyzer 62 includes an information processing unit 52, a measurement unit 42, and a sample supplying section 32b (see FIG. 7) being a part of the transporting unit 32. The sample processing system 1 is communicably connected to a host computer 8 via a communication network.

The feeding unit 21, the tube sorter 22, the relay unit 23, the relay unit 24, the collection unit 25, and the transporting units 31 to 33 are arranged adjacent to each other in the left-right direction such that a sample rack L can be transported therebetween. Further, each of the units and apparatus is configured such that a plurality of sample racks L, each being capable of holding ten sample tubes T, can be placed thereon, and such that each sample rack L can be transported along the arrows in FIG. 1.

FIGS. 2A and 2B show structures of a sample tube T and a sample rack L, respectively. FIG. 2A is a perspective view showing an external view of a sample tube T, and FIG. 2B is a perspective view showing an external view of a sample rack L holding ten sample tubes T. FIG. 2B also shows the orientation (front, rear, left, and right directions shown in FIG. 1) of the sample rack L when it is transported.

With reference to FIG. 2A, each sample tube T is a tubular container made of glass or synthetic resin having translucency, and its upper end is open. A bar code label T1 is attached to a lateral surface of the sample tube T. A bar code including a sample ID is printed on the bar code label T1. The sample tube T contains a whole blood sample collected from a patient, and the opening at the upper end thereof is sealed with a rubber cap T2.

With reference to FIG. 2B, a bar code label L1 is attached to a lateral surface on the rear side of the sample rack L. A bar code including a rack ID is printed on the bar code label L1. Further, holders capable of vertically holding ten sample tubes T are formed in the sample rack L. Hereinafter, for convenience, the positions of the holders are referred to as holding positions 1 to 10, from downstream to upstream in the transport direction, in the ascending order.

With reference back to FIG. 1, when starting measurement of sample(s), a user sets one or more sample tubes T each containing a sample on a sample rack L, and places this sample rack L in the feeding unit 21. When supplying an empty sample rack L to an empty rack stocker 110 of the tube sorter 22, the user places the empty sample rack L in the feeding unit 21. The sample rack L placed in the feeding unit 21 is transported rearward, and sent out to the tube sorter 22.

The tube sorter 22 includes therein a bar code unit B, the empty rack stocker 110, a buffer rack 120, six archive racks R1, a sorting rack R2, and a display input section 22a composed of a touch panel having a displaying function and an inputting function integrated therein. As described later, each of the buffer rack 120, the archive racks R1, and the sorting rack R2 includes a plurality of holders for holding sample tubes T. It should be noted that the tube sorter 22 is provided with a lid (not shown) that covers the front face and the upper face thereof, and the user can access the inside of the tube sorter 22 by opening the lid.

The tube sorter 22 first performs a process by the bar code unit B, with respect to a sample rack L that has been sent out from the feeding unit 21 to the tube sorter 22. Specifically, the bar code unit B reads a rack ID from the bar code label L1 of the sample rack L, detects holding position(s) at which the one or more sample tubes T are held in the sample rack L, and reads a sample ID from the bar code label T1 of each sample tube T. The structure of the bar code unit B will be described later with reference to FIGS. 4A and 4B.

Subsequently, the tube sorter 22 transmits each sample ID read by the bar code unit B to the host computer 8 via the transport controller 7, and receives information (hereinafter, referred to as "transfer information") for transferring a corresponding sample tube T within the tube sorter 22, from the host computer 8 via the transport controller 7. The transfer information will be described later with reference to FIGS. 10A and 10B.

Subsequently, in accordance with the received piece(s) of transfer information, the tube sorter 22 transfers sample tube(s) T held in the sample rack L, to the buffer rack 120, the archive racks R1, or the sorting rack R2. In a case where the transportation destination of a sample tube T is the measurement unit 41, transfer of this sample tube T is not performed. In a case where the transportation destination of a sample tube T is the measurement unit 42 or the smear preparing apparatus 63, this sample tube T is transferred to the buffer rack 120. In a case where the bar code unit B has failed in reading a sample ID, or in a case where the transportation destination of the sample corresponding to a sample ID is none of the measurement units 41 and 42, and the smear preparing apparatus 63, this sample tube T is transferred to the sorting rack R2. Moreover, as described later, sample tubes T for which measurement and preparation of a smear have been completed are transferred to the archive racks R1.

After the transfer operation for sample tube(s) T, in a case where one or more sample tubes T remain in this sample rack L, this sample rack L is sent out to the relay unit 23. On the other hand, in a case where all of the sample tube(s) T have been unloaded and the sample rack L has become empty, and in a case where the sample rack L has been empty from the beginning, this sample rack L is stocked in the empty rack stocker 110 if the empty rack stocker 110 has a vacancy, or is sent out to the relay unit 23 if the empty rack stocker 110 is full. Into an empty sample rack L, one or more sample tubes T which have been held in the buffer rack 120 are set at a predetermined timing. The sample rack L in which the one or more sample tubes T are set is sent out to the relay unit 23. Transportation of the sample rack L by the tube sorter 22 will be described later with reference to FIG. 9 and subsequent figures.

A sample rack L sent out from the tube sorter 22 to the relay unit 23 and holding one or more sample tubes T is sent out to the relay unit 24. On the other hand, a sample rack L holding no sample tube T is transported forward in the relay unit 23. The sample rack L sent out from the relay unit 23 to the relay unit 24 is transported forward in the relay unit 24, and then, sent out to the transporting unit 31.

To the rear of the transporting units 31, 32, and 33, the measurement unit 41, the measurement unit 42, and the smear preparing apparatus 63 are arranged, respectively. Each of the transporting units 31 to 33 transports a sample rack L sent out from the upstream side, in accordance with an instruction from the transport controller 7. Specifically, each of the transporting units 31 to 33 transports, in a case where processing is performed in its corresponding unit or apparatus, a sample rack L sent out from the upstream side, rearward, to transport the sample rack L to a front position facing its corresponding unit or apparatus. In a case where processing is not performed in the measurement units 41 and 42, each of the transporting units 31 and 32 causes a sample rack L sent out from the upstream side, to advance directly leftward, and sequentially sends it out to its downstream transporting unit.

Each of the measurement units 41 and 42 takes a sample tube T out of the sample rack L transported to its front position, and measures the sample contained in this sample tube T. Specifically, each of the measurement units 41 and 42 moves the sample tube T taken out of the sample rack L rearward, to take it therein, aspirates the sample from this sample tube T, and measures the aspirated sample. Upon completion of the measurement, each of the measurement units 41 and 42 returns this sample tube T to its original holder of the sample rack L.

The information processing units 51 and 52 are communicably connected to the measurement units 41 and 42, respectively, and control the measurement units 41 and 42, respectively. Each of the information processing unit 51 and 52 receives measurement data of a sample from the corresponding one of the measurement units 41 and 42 to analyze the measurement data, and generates an analysis result containing analysis values of respective measurement items. Further, the information processing units 51 and 52 are communicably connected to the host computer 8 and transmit analysis results to the host computer 8.

The smear preparing apparatus 63 aspirates, at its front position, a sample from a sample tube T held in a sample rack L, and prepares a smear of the aspirated sample. The smear preparing apparatus 63 is communicably connected to the host computer 8, and transmits to the host computer 8 information indicating that smear preparation has been completed.

When the processing by each of the measurement units 41 and 42 and the smear preparing apparatus 63 has been completed, and there is no need to perform processing on the downstream side any more, each sample rack L is transported forward in the measurement unit where the sample rack L is being transported, and then sent out to the upstream side by this measurement unit. In this manner, each sample rack L is sequentially transported to the upstream side.

The sample rack L is transported in the upstream direction from the transporting units 31 to 33 to the feeding unit 21 via the relay units 23, relay unit 24 and front transport path of the tube sorter 22. When the sample rack L arrives the feeding unit 21, it is transported rearward in the feeding unit 21, and then sent out to the tube sorter 22 again. Also in this case, similarly to the above, detection and reading are performed by the bar code unit B, and the one or more sample tubes T held in the sample rack L are transferred in accordance with their transfer information. In the present embodiment, depending on the result of a first measurement (first test) of a sample performed by the measurement unit 41 or 42, there may be a case where a second measurement (retest) of the same sample is performed by the measurement unit 41 or 42 or smear preparation is performed by the smear preparing apparatus 63. A sample tube T which does not need re-processing (retest by the measurement unit 41 or 42 or smear preparation by the smear preparing apparatus 63) is transferred to one of the archive racks R1. Also in this case, a sample rack L from which the one or more sample tubes T have been all unloaded and which has become empty is stocked in the empty rack stocker 110 if the empty rack stocker 110 has a vacancy, or sent out to the relay unit 23 if the empty rack stocker 110 is full.

The empty sample rack L sent out from the tube sorter 22 to the relay unit 23 is transported forward in the relay unit 23, and then sent out to the tube sorter 22. This sample rack L is transported rightward by the tube sorter 22 and the feeding unit 21, and sent out to the collection unit 25. Then, the sample rack L is transported rearward in the collection unit 25 to be housed in the collection unit 25. Thus, transportation of the sample rack L is completed.

The transport controller 7 is communicably connected to the feeding unit 21, the tube sorter 22, the relay unit 23, the relay unit 24, the collection unit 25, a sample relaying section 31*a* (see FIG. 7) being a part of the transporting unit 31, a sample relaying section 32*a* (see FIG. 7) being a part of the transporting unit 32, and the transporting unit 33, and controls transporting operations of a sample rack L performed by these. Further, the transport controller 7 is communicably connected to the host computer 8. Upon receiving from the tube sorter 22 information obtained by the bar code unit B, the transport controller 7 transmits each sample ID to the host computer 8. Then, the transport controller 7 receives from the host computer 8 a measurement order and transfer information corresponding to each sample ID, and transmits the transfer information to the tube sorter 22.

The host computer 8 has stored therein, associated with each sample ID, a measurement order of the sample corresponding to the sample ID and analysis results of this sample. Moreover, the host computer 8 retains a rule for transferring a sample tube T within the tube sorter 22. Upon receiving a sample ID from the transport controller 7, the host computer 8 creates transfer information indicating how the sample tube T corresponding to the sample ID is transferred in the tube sorter 22, and transmits the created transfer information to the transport controller 7.

Figure 3:
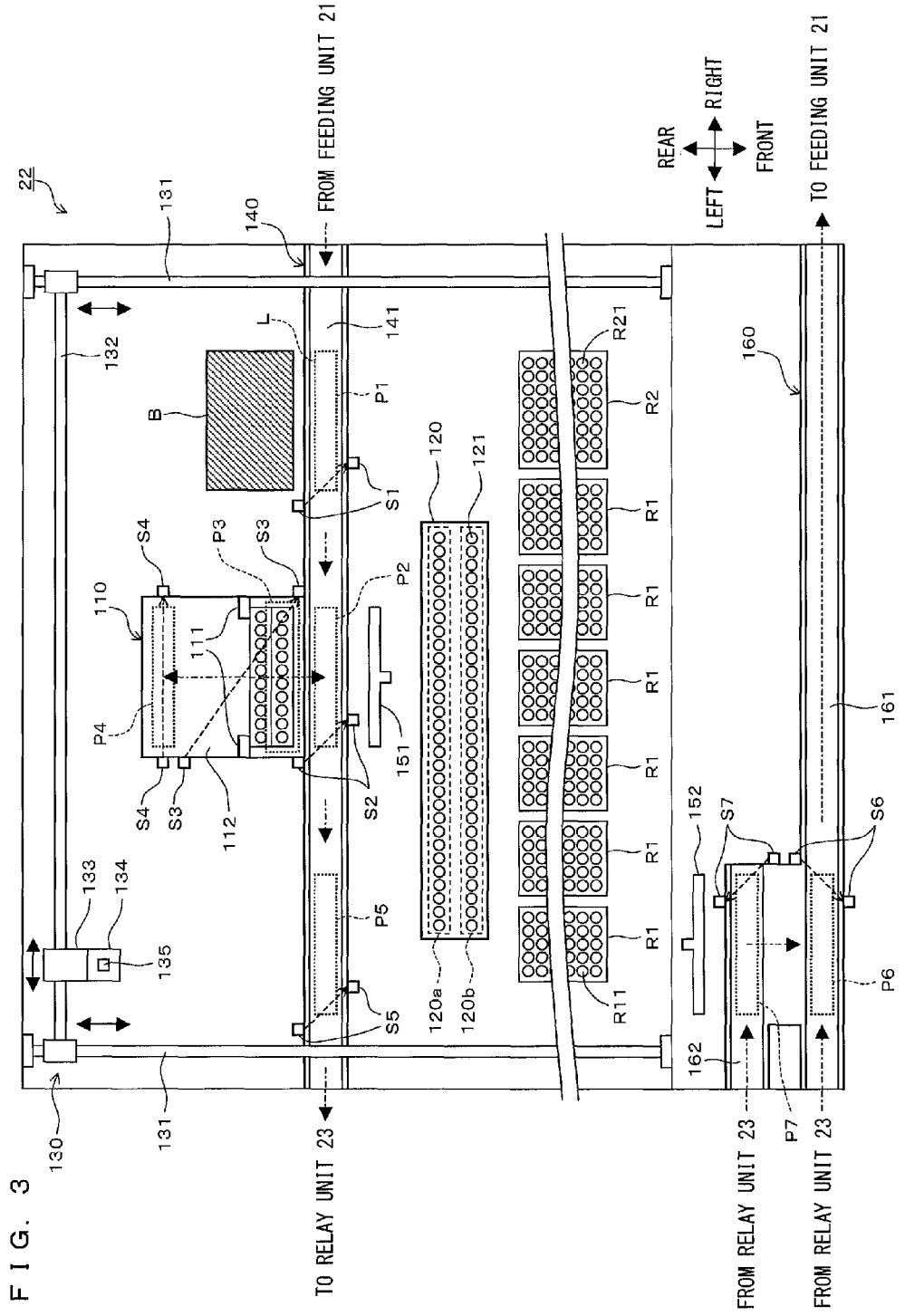
FIG. 3 shows a structure of the inside of a tube sorter according to an embodiment, viewed from above.

FIG. 3 shows a structure of the inside of the tube sorter 22 viewed from above.

The tube sorter 22 is provided with a tube conveyor 130 for conveying a sample tube T within the tube sorter 22. The tube conveyor 130 includes: two guides 131 fixed inside the tube sorter 22 and extending in the front-rear direction; a guide 132 extending in the left-right direction and slidable in the front-rear direction along the guides 131; a sliding part 133 slidable in the left-right direction along the guide 132; an ascending/descending part 134 set in the sliding part 133 and capable of ascending/descending relative to the sliding part 133; a gripper 135 set at the lower end of the ascending/descending part 134 and capable of gripping a sample tube T; and a mechanism for driving these parts. It should be noted that the guides 131 are located at a higher level than a transport path 140.

The buffer rack 120 is provided with 60 holders 121. In the buffer rack 120, a region 120*a* including 30 holders 121 on the rear side and a region 120*b* including 30 holders 121 on the front side are set. Each archive rack R1 is provided with 125 holders R11, and the sorting rack R2 is provided with 250 holders R21.

A sample rack L sent out from the feeding unit 21 is transported leftward by a belt 141 of the transport path 140 to be located at a position P1 facing the bar code unit B. The sample rack L located at the position P1 is detected by a sensor S1. The bar code unit B detects holding position(s) at which respective sample tube(s) T are held in the sample rack L, and also reads the rack ID and their sample ID(s).

Figure 4B:
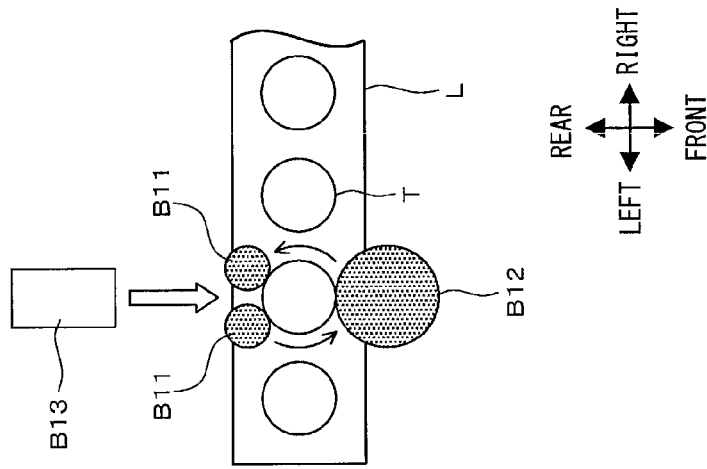
FIG. 4B illustrates a reading operation performed by a bar code unit according to an embodiment.
Figure 4A:
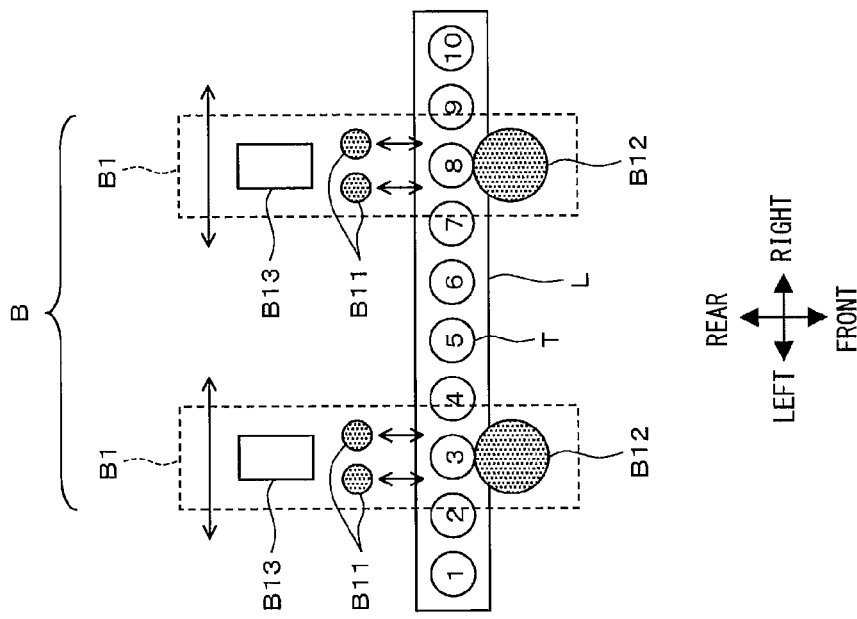
FIG. 4A illustrates a reading operation performed by a bar code unit according to an embodiment.

FIG. 4A illustrates a reading operation performed by the bar code unit B.

The bar code unit B includes two moving parts B1 provided in the left-right direction. Each of the two moving parts B1 is configured to be able to move in the left-right direction, and includes two rollers B11, a roller B12, and a bar code reader B13. Each bar code reader B13 is fixed to its corresponding moving part B1, and reads a rack ID and sample IDs from the bar code labels L1 and T1 located in front thereof.

The left moving part B1 is sequentially moved to positions corresponding to holding positions 1 to 5, and the right moving part B1 is sequentially moved to positions corresponding to holding positions 6 to 10. As shown in FIG. 4B, at each holding position, the moving part B1 moves the rollers B11 forward. At this time, if the rollers B11 are moved further forward than the distance at which the rollers B11 should abut against a sample tube T, it is detected that no sample tube T exists at the holding position. If the rollers B11 abut against a sample tube T, the roller B12 are rotated, and the bar code label T1 is read.

With reference back to FIG. 3, upon completion of detection and reading by the bar code unit B, the sample rack L is transported leftward to be located at a position P2. The sample rack L located at the position P2 is detected by a sensor S2. With the sample rack L being located at the position P2, sample tube(s) T held in this sample rack L are transferred by the tube conveyor 130 in accordance with their transfer information.

The transfer information includes a transfer destination within the tube sorter 22 of a sample tube T. Specifically, the transfer information is any of "transfer unnecessary", "buffer rack region 120a", "buffer rack region 120b", "archive rack", and "sorting rack". When the transfer information of a sample tube T is "buffer rack region 120a", "buffer rack region 120b", "archive rack", or "sorting rack", this sample rack L is accordingly transferred to a holder 121 of the region 120a of the buffer rack 120, a holder 121 of the region 120b of the buffer rack 120, a holder R11 of one of the archive racks R1, or a holder R21 of the sorting rack R2.

The empty rack stocker 110 is provided so as to be connected to the transport path 140 at the position P2 of the transport path 140, with a width greater than the width in the longitudinal direction of a sample rack L (the width in the left-right direction shown in FIG. 2B).

An empty sample rack L located at the position P2 is, when it is to be conveyed into the empty rack stocker 110, pushed out to a position P3, which is in a front portion of the empty rack stocker 110, by the front side face of the sample rack L being pushed by a rack pushing-out mechanism 151. The sample rack L located at the position P3 is detected by a sensor S3. On the other hand, a sample rack L located at the position P3 is sent to the position P2, by the rear side face of the rearmost sample rack L in the empty rack stocker 110 being pushed by a rack sending-in mechanism 111.

Here, the empty rack stocker 110 can stock up to six sample racks L. When six sample racks L are stocked in the empty rack stocker 110 and the empty rack stocker 110 becomes full, the rearmost sample rack L is located at a position P4. The sample rack L located at the position P4 is detected by a sensor S4.

FIG. 5 is a perspective view showing a vicinity of a part where the empty rack stocker 110 is connected to the transport path 140. It should be noted that the sensors S2 to S4 and the rack sending-in mechanism 111 are not shown for convenience.

The transport path 140 includes a wall 142 extending in the left-right direction and provided to the front of the belt 141, and walls 143 and 144 extending in the left-right direction and provided to the rear of the belt 141. The walls 142 to 144 protrude upward relative to the upper face of the belt 141. Accordingly, the sample rack L is transported in the left-right direction by the belt 141, without tilting in the front-rear direction.

In addition, an opening 142a is formed in the wall 142, in front of the position P2, and the distance between the walls 143 and 144 is longer than the width in the longitudinal direction of the sample rack L. Accordingly, the rack pushing-out mechanism 151 can push out the front side face of the sample rack L at the position P2, via the opening 142a, and can push out this sample rack L rearward through the gap between the walls 143 and 144 toward the empty rack stocker 110. Further, at this time, the sample rack L is pushed out in a direction (rearward direction) that crosses the transport direction (leftward direction) of the transport path 140. Accordingly, the empty sample rack L is quickly transported to the empty rack stocker 110.

The empty rack stocker 110 includes a storage region 112 whose upper face is a horizontal surface, and walls 113, 114, and 115 which are respectively provided at the rear end, right end, and left end of the storage region 112. The walls 113 to 115 protrude upward relative to the upper face of the storage region 112, and the storage region 112 is defined by the walls 113 to 115. Accordingly, the sample rack L can move in the front-rear direction while sliding on the storage region 112, between the position P2 and the position P4, without going out of the storage region 112.

With reference to back to FIG. 3, the sample rack L located at the position P2 is, when it is to be conveyed to the downstream side, transported leftward by the belt 141 to be located at a position P5. The sample rack L located at the position P5 is detected by a sensor S5. The sample rack L located at the position P5 is transported leftward by the belt 141 to be sent out to the relay unit 23.

Here, a sample rack L that holds only sample tube(s) T that were not transferred at the position P2 is transported to the measurement unit 41, and is subjected to measurement by the measurement unit 41. Meanwhile, one or more sample tubes T held in the region 120a of the buffer rack 120 are transferred, as appropriate, to an empty sample rack L located at the position P2. Then, this sample rack L is transported to the measurement unit 42 and is subjected to measurement by the measurement unit 42. Further, one or more sample tubes T held in the region 120b of the buffer rack 120 are transferred, as appropriate, to an empty sample rack L located at the position P2. Then, this sample rack L is transported to the smear preparing apparatus 63 and is subjected to smear preparation by the smear preparing apparatus 63. That is, the regions 120a and 120b are regions for temporarily holding sample tubes T to be transported to the measurement unit 42 and the smear preparing apparatus 63, respectively, and one or more sample tubes T that remain in a sample rack L without being transferred to these regions are transported to the measurement unit 41, and are subjected to measurement by the measurement unit 41.

Next, a sample rack L sent out from the relay unit 23 to a transport path 160 is transported rightward by a belt 161 of the transport path 160 or a belt 162, and is located at a position P6 or a position P7. The sample rack L located at the position P6 or P7 is detected by a sensor S6 or S7, respectively. The sample rack L at the position P7 is then located to the position P6, by the rear side face of the sample rack L being pushed by a rack pushing-out mechanism 152. The sample rack L located at the position P6 is transported rightward by the belt 161, to be sent out to the feeding unit 21.

Figure 6:
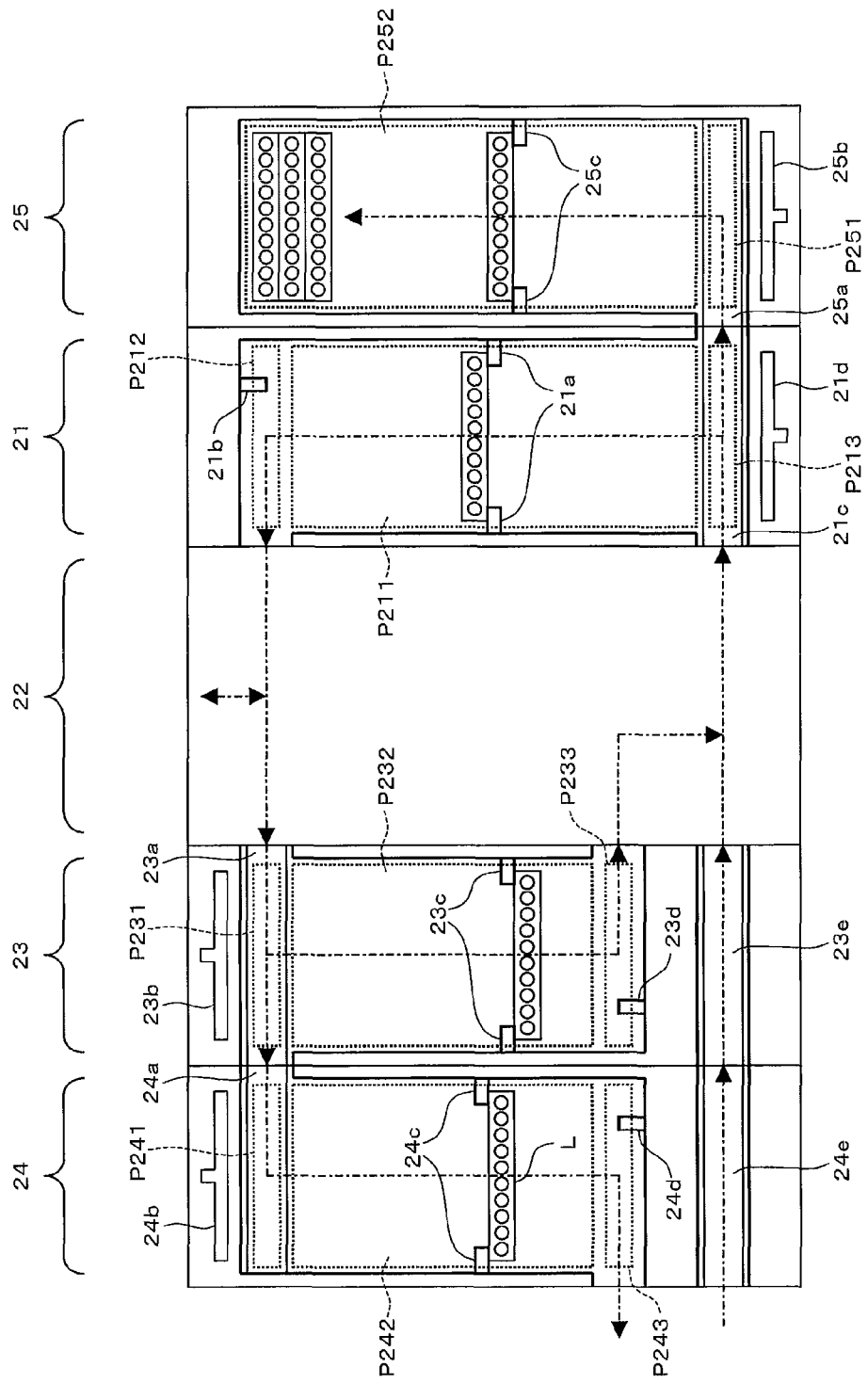
FIG. 6 shows structures of a feeding unit, a relay unit, another relay unit, and a collection unit according to embodiment, viewed from above.

FIG. 6 shows structures of the feeding unit 21, the relay unit 23, the relay unit 24, and the collection unit 25, viewed from above. It should be noted that the inside of the tube sorter 22 is not shown for convenience.

When a sample rack L is located at a position P211 of the feeding unit 21, this sample rack L is then located at a position P212 by a rack sending-in mechanism 21a, and then sent out by a rack sending-out mechanism 21b to the tube sorter 22. On the other hand, a sample rack L sent out from the tube sorter 22 to the feeding unit 21 is located at a position P213 by a belt 21c. In a case where one or more sample tubes T are held in a sample rack L located at the position P213, this sample rack L is pushed out to the position P211 by a rack pushing-out mechanism 21d. In a case where the sample rack L located at the position P213 is empty, this sample rack L is transported to the collection unit 25 by the belt 21c.

The sample rack L sent out from the tube sorter 22 to the relay unit 23 is located at a position P231 by a belt 23a. In a case where one or more sample tubes T are held in the sample rack L located at the position P231, this sample rack L is transported to the relay unit 24 by the belt 23a. In a case where the sample rack L located at the position P231 is empty, this sample rack L is pushed out to a position P232 by a rack pushing-out mechanism 23b, then located at a position P233 by a rack sending-in mechanism 23c, and then sent out to the tube sorter 22 by a rack sending-out mechanism 23d. On the other hand, a sample rack L sent out from the relay unit 24 to the relay unit 23 is sent out to the tube sorter 22 by a belt 23e.

The sample rack L sent out from the relay unit 23 to the relay unit 24 is located at a position P241 by a belt 24a, then located at a position P242 by a rack pushing-out mechanism 24b, then located at a position P243 by a rack sending-in mechanism 24c, and then sent out to the transporting unit 31 by a rack sending-out mechanism 24d. On the other hand, a sample rack L sent out from the transporting unit 31 to the relay unit 24 is sent out to the relay unit 23 by a belt 24e.

A sample rack L sent out from the feeding unit 21 to the collection unit 25 is located at a position P251 by a belt 25a, then pushed out to a position P252 by a rack pushing-out mechanism 25b, and then housed in a rear portion of the position P252 by a rack sending-in mechanism 25c.

Figure 7:
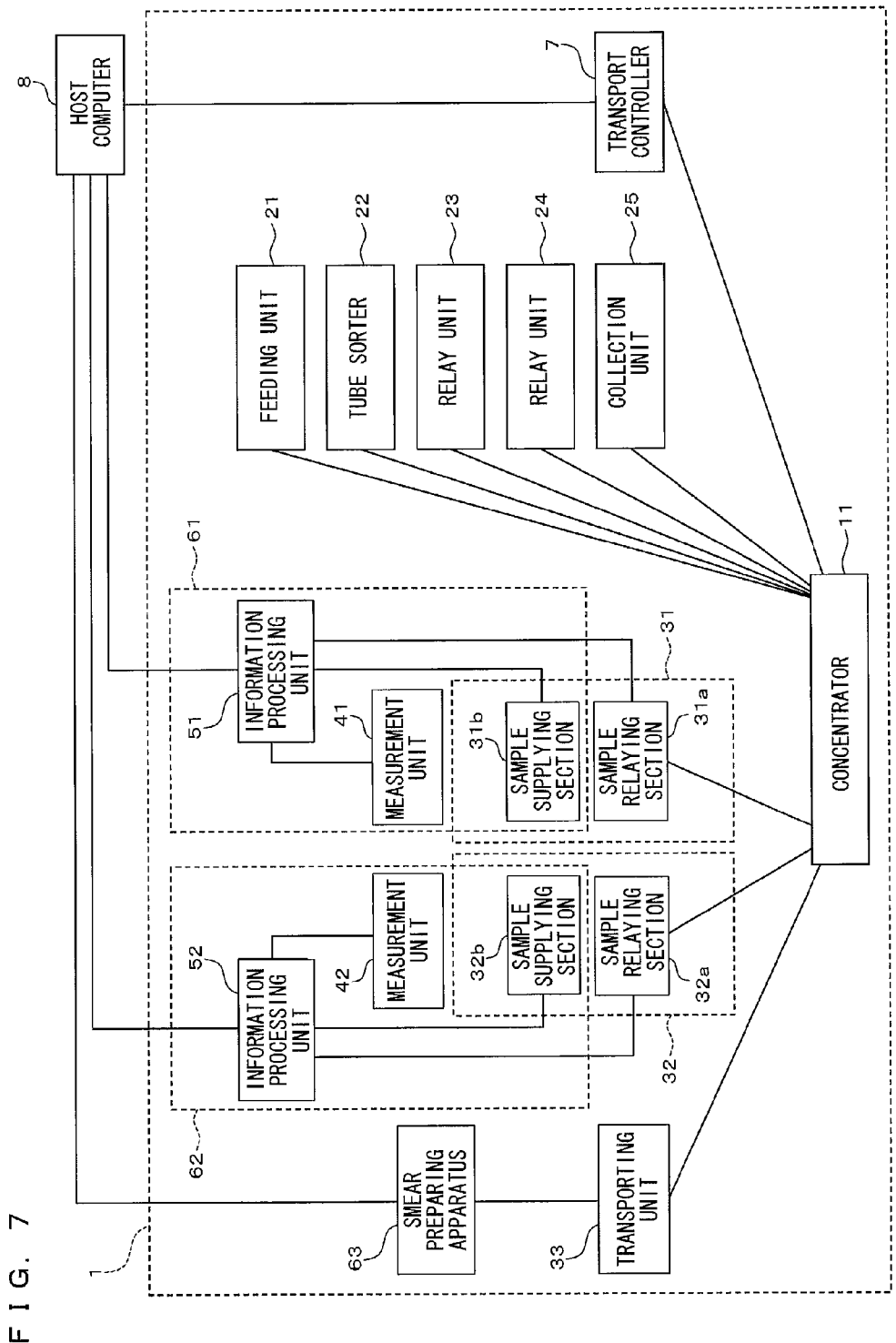
FIG. 7 shows mutual connection relationship between units and apparatuses in the sample processing system according to an embodiment.

FIG. 7 shows mutual connection relationship between units and apparatuses in the sample processing system 1.

The transporting unit 31 is shown, divided into the sample relaying section 31a and the sample supplying section 31b. The transporting unit 32 is shown, divided in the sample relaying section 32a and the sample supplying section 32b. The sample supplying sections 31b and 32b respectively include parts that transport sample racks L to front positions facing the measurement units 41 and 42, respectively.

The feeding unit 21, the tube sorter 22, the relay unit 23, the relay unit 24, the collection unit 25, the sample relaying sections 31a and 32a, the transporting unit 33, and the transport controller 7 are communicably connected to a concentrator 11. The information processing unit 51 is communicably connected to the sample relaying section 31a, the sample supplying section 31b, and the measurement unit 41. The information processing unit 52 is communicably connected to the sample relaying section 32a, the sample supplying section 32b, and the measurement unit 42. The smear preparing apparatus 63 is communicably connected to the transporting unit 33.

Figure 8:
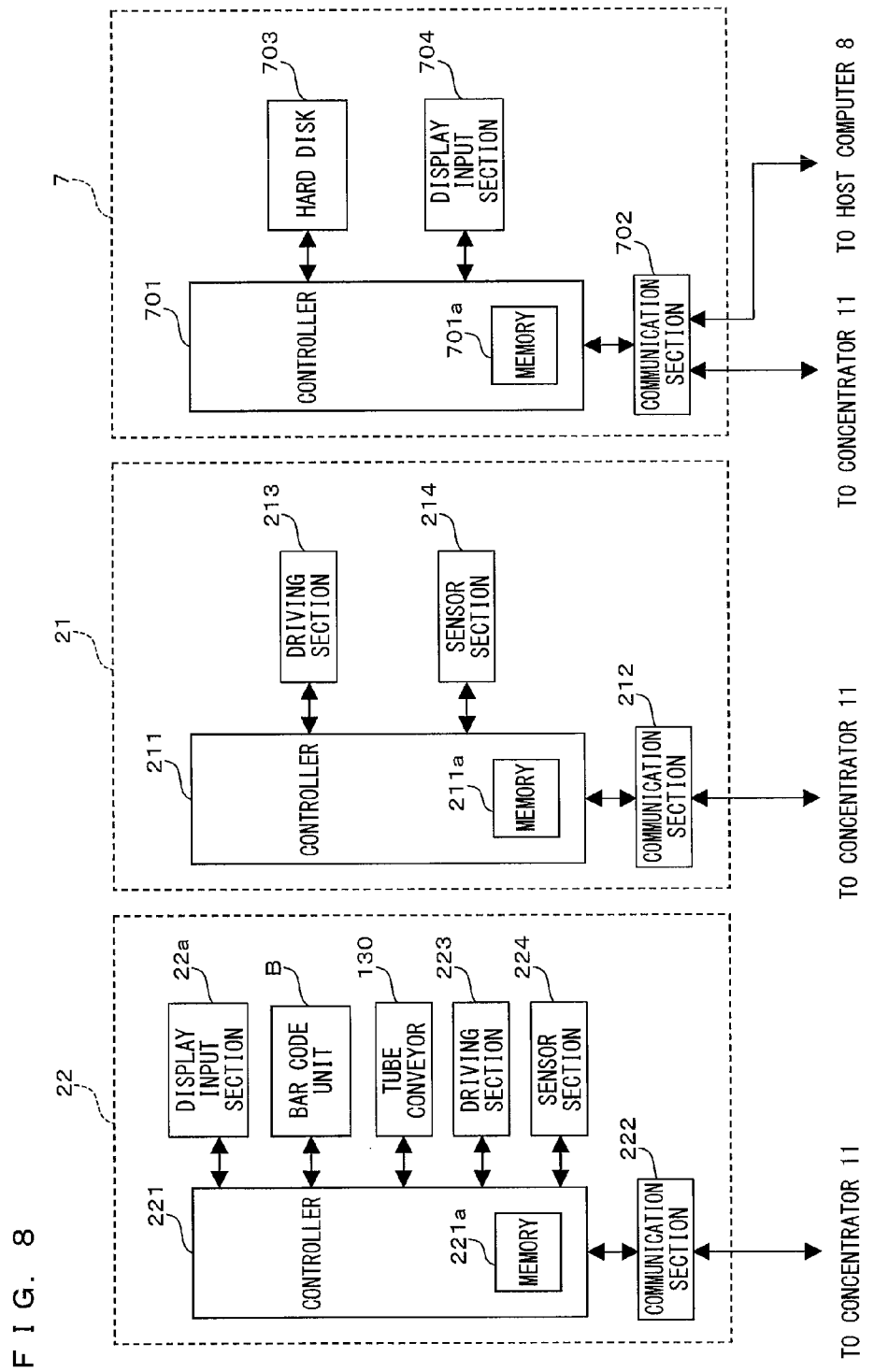
FIG. 8 shows schematic configurations of the feeding unit, the tube sorter, and a transport controller according to an embodiment.

FIG. 8 shows schematic configurations of the feeding unit 21, the tube sorter 22, and the transport controller 7.

The tube sorter 22 includes a controller 221, a communication section 222, the display input section 22a, the bar code unit B, the tube conveyor 130, a driving section 223, and a sensor section 224. The controller 221 includes a memory 221a. The controller 221 controls these components in the tube sorter 22 by executing computer programs stored in the memory 221a, and receives signals outputted from these components in the tube sorter 22. Further, the controller 221 communicates with the transport controller 7 via the communication section 222.

The memory 221a has stored therein information of whether a sample tube T is held in each holder of the buffer rack 120, the archive racks R1, and the sorting rack R2, and the sample ID of the sample tube T held therein, associated with each other. Moreover, the memory 221a has stored therein a first sending-out request flag and a second sending-out request flag respectively set for the region 120a and the region 120b of the buffer rack 120. The first sending-out request flag is a flag indicating whether a sample tube T held in the region 120a needs to be immediately sent out, using an empty sample rack L. The second sending-out request flag is a flag indicating whether a sample tube T held in the region 120b needs to be immediately sent out, using an empty sample rack L.

The driving section 223 includes mechanisms for driving the belts 141, 161, and 162, the rack pushing-out mechanisms 151 and 152, and the rack sending-in mechanism 111 shown in FIG. 3, and in addition, a mechanism for transporting a sample rack L in the tube sorter 22, and a drive source for driving these mechanisms. The sensor section 224 includes the sensors S1 to S7 shown in FIG. 3, and in addition, a sensor for detecting a sample rack L in the tube sorter 22.

The feeding unit 21 includes a controller 211, a communication section 212, a driving section 213, and a sensor section 214. The controller 211 includes a memory 211a. The feeding unit 21 has substantially the same configuration as that of the tube sorter 22 from which the bar code unit B and the tube conveyor 130 are omitted, and thus, description thereof is omitted here. It should be noted that the relay unit 23, the relay unit 24, and the collection unit 25 have configurations similar to that of the feeding unit 21.

The transport controller 7 includes a controller 701, a communication section 702, a hard disk 703, and a display input section 704. The controller 701 includes a memory 701a. The controller 701 communicates with the feeding unit 21, the tube sorter 22, the relay unit 23, the relay unit 24, the collection unit 25, the sample relaying sections 31a and 32a, the transporting unit 33, and the host computer 8, via the communication section 702.

Figure 9:
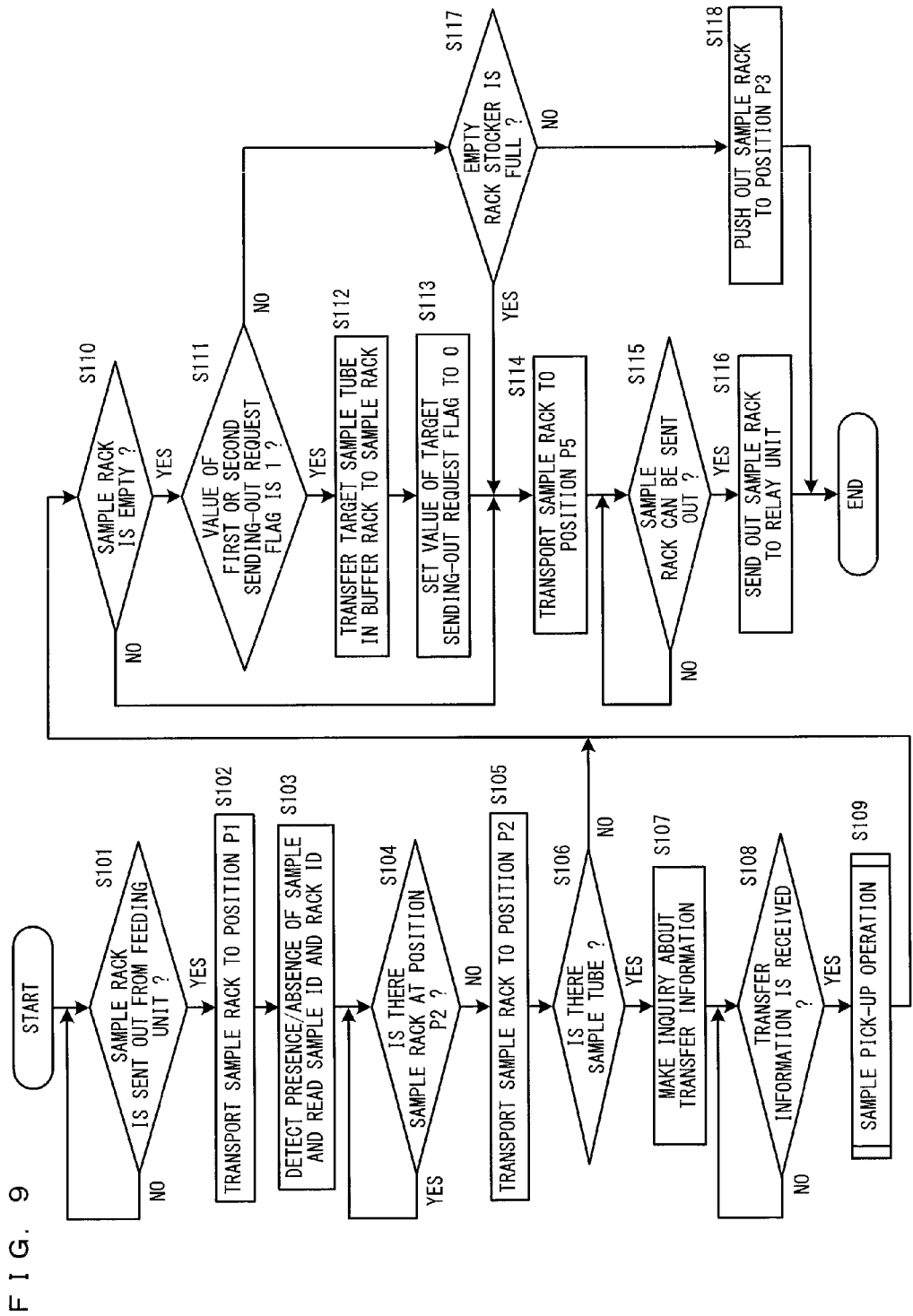
FIG. 9 is a flow chart showing a transport process for a sample rack sent out from the feeding unit to the tube sorter according to an embodiment.

FIG. 9 is a flow chart showing a transport process for a sample rack L sent out from the feeding unit 21 to the tube sorter 22. At the activation of the tube sorter 22, 0 is set to each of the values of the first sending-out request flag and the second sending-out request flag stored in the memory 221a.

When a sample rack L located at the position P212 of the feeding unit 21 is sent out to the transport path 140 (S101: YES), the controller 221 of the tube sorter 22 causes this sample rack L to be transported to the position P1 (S102). Subsequently, the controller 221 causes the bar code unit B to detect presence or absence of sample tube T with regards to respective holding position(s) of this sample rack L. And the controller 221 causes the barcode unit B to read the sample IDs and the rack ID (S103). Subsequently, if there is no preceding sample rack L at the position P2 (S104: NO), the controller 221 causes the sample rack L at the position P1 to be transported to the position P2 (S105).

Next, based on the detection of the presence/absence of sample tubes T in S103, the controller 221 determines whether one or more sample tubes T are held in this sample rack L (S106). If this sample rack L is empty (S106: NO), the processing is advanced to S110. On the other hand, if one or more sample tubes T are held in this sample rack L (S106: YES), the controller 221 transmits the sample ID of each held sample tube T to the transport controller 7, thereby making inquiry about transfer information (S107).

As described above, upon receiving a sample ID from the tube sorter 22, the transport controller 7 transmits the received sample ID to the host computer 8. Further, upon receiving transfer information of the sample tube T from the host computer 8, the transport controller 7 transmits to this information to the tube sorter 22. The controller 221 causes the processing to wait until receiving all sample transfer information which has been inquired about (S108).

FIGS. 10A and 10B each shows a concept of an example of obtained transfer information.

In a sample rack L of the example shown in FIG. 10A, sample tubes T are held in holding positions 1 to 9, and no sample tube T is held in holding position 10. The bar code unit B has read sample IDs of the sample tubes T at holding positions 1 to 8 but has failed in reading the sample ID of the sample tube T at holding position 9. It is assumed that: with respect to the sample IDs corresponding to holding positions 1 to 5, the host computer 8 retains measurement orders to be executed in the measurement unit 41; with respect to the sample IDs corresponding to holding position 6, the host computer 8 retains a measurement order to be executed in the measurement unit 42; and with respect to the sample ID corresponding to holding position 7, the host computer 8 retains a measurement order to be executed in the smear preparing apparatus 63. With respects to the sample ID corresponding to holding position 8, the host computer 8 retains no measurement order to be performed in any of the measurement units 41, 42 and smear preparing apparatus 63.

In this case, since reading of the sample ID of the sample tube T at holding position 9 has been failed, the controller 221 of the tube sorter 22 determines the sorting rack R2 as the destination of this sample tube T and sets transfer information of this sample tube T to "sorting rack". Then, the controller 221 transmits the sample IDs corresponding to holding positions 1 to 8, to the host computer 8. Based on the received sample IDs, the host computer 8 creates transfer information of the sample tubes T.

The host computer 8 stores measurement orders to be executed for each of samples. For the sample IDs corresponding to holding positions 1 to 5, the host computer 8 stores measurement orders to be executed in the measurement unit 41. For the sample ID corresponding to holding position 6, the host computer 8 stores a measurement order to be executed in the measurement unit 42. And for the sample ID corresponding to holding position 7, the host computer 8 stores a measurement order to be executed in the smear preparing apparatus 63. According to the stored measurement orders, the host computer 8 sets transfer information for the sample IDs corresponding to holding positions 1 to 5, transfer information for the sample ID corresponding to holding position 6, and transfer information for the sample ID corresponding to holding position 7, to "transfer unnecessary", "buffer rack region 120a", and "buffer rack region 120b", respectively. Since the host computer 8 does not retain measurement order of the sample ID corresponding to holding position 8, the host computer 8 determines the destination of the sample of holding position 8 to the sorting rack R2. The host computer 8 sets transfer information for the sample ID corresponding to holding position 8 to "sorting rack".

Upon creating transfer information as described above, the host computer 8 transmits these pieces of information to the tube sorter 22. Then, the controller 221 of the tube sorter 22 receives transfer information corresponding to holding positions 1 to 8, and thus obtains transfer information of all the held sample tubes T as shown in FIG. 10A.

In a sample rack L of the example shown in FIG. 10B, sample tubes T are held at holding positions 1 to 5, and no sample tubes T are held at holding positions 6 to 10. Further, the bar code unit B has read the sample IDs of the sample tubes T at holding positions 1 to 5. Further, it is assumed that, with respect to each of the sample IDs corresponding to holding positions 1 to 5, the host computer 8 retains analysis results received from the measurement unit 41 or 42, or information of completion of smear preparation that has been received from the smear preparing apparatus 63.

Also in this case, similarly to the case above, the controller 221 of the tube sorter 22 transmits the sample IDs corresponding to holding positions 1 to 5, to the host computer 8. Based on the received sample IDs, the host computer 8 creates transfer information of the sample tubes T.

Specifically, in a case where the host computer 8 retains analysis results or information of completion of smear preparation, for the sample IDs corresponding to holding positions 1 to 5, the host computer 8 sets transfer information of these sample IDs to "archive rack". In a case where the host computer 8 retains an analysis result from the measurement unit 41 or 42, and if the host computer 8 has determined that re-processing at the measurement unit 41 or 42 or the smear preparing apparatus 63 is necessary, the host computer 8 sets transfer information of the sample ID corresponding to this analysis result to "transfer unnecessary", "buffer rack region 120a", or "buffer rack region 120b".

Upon creating pieces of transfer information as described above, the host computer 8 transmits these pieces of information to the tube sorter 22. As a result, the controller 221 of the tube sorter 22 receives the pieces of transfer information corresponding to holding positions 1 to 5, and thus obtains transfer information of all the held sample tubes T as shown in FIG. 10B.

With reference back to FIG. 9, upon completion of obtainment of the transfer information, the controller 221 causes an sample pick-up operation to be performed on the sample rack L being at the position P2 and holding the one or more sample tubes T (S109). As a result, one or more sample tubes T held in this sample rack L are transferred to the buffer rack 120, the archive racks R1, or the sorting rack R2, as necessary.

FIG. 11 is a flow chart showing the sample pick-up operation. In the sample pick-up operation, processes of S201 to S213 are sequentially performed for the ten holding positions.

When there is a sample tube T at a holding position, in the sample rack L, referred to by the controller 221 of the tube sorter 22 (S201: YES), the controller 221 transfers as appropriate the sample tube T as described below, based on its transfer information (S202 to S213). In transferring a sample tube T, the controller 221 controls the tube conveyor 130. When there is no sample tube T at the holding position referred to, the processing is advanced to S214.

When the transfer information of the sample tube T is "transfer unnecessary" (S202: YES), the controller 221 does not cause this sample tube T to be transferred, and the processing is advanced to S214. When the transfer information of the sample tube T is "buffer rack region 120a" (S202: NO, S203: YES), if there is a vacant holder 121 in the region 120a (S204: YES), the controller 221 causes this sample tube T to be transferred to the holder 121 in the region 120a (S205). When the transfer information of the sample tube T is "buffer rack region 120b" (S202, S203: NO, S206: YES), if there is a vacant holder 121 in the region 120b (S207: YES), the controller 221 causes this sample tube T to be transferred to the holder 121 in the region 120b (S208). When the transfer information of the sample tube T is "sorting rack" (S202, S203, S206: NO, S209: YES), if there is a vacant holder R21 in the sorting rack R2 (S210: YES), the controller 221 causes this sample tube T to be transferred to the holder R21 in the sorting rack R2 (S211). When the transfer information of the sample tube T is "archive rack" (S202, S203, S206, S209: NO), if there is a vacant holder R11 in the archive racks R1 (S213: YES), the controller 221 causes this sample tube T to be transferred to the holder R11 in the archive racks R1 (S209). When there is no vacancy in the transfer destination (S204, S207, S210, S212: NO), no transfer is performed and the processing is advanced to S214.

The controller 221 performs the processes of S201 to S213 for all the holding positions in the sample rack L, and when all the processes have completed (S214: YES), the sample pick-up operation ends.

It should be noted that, in a case where there was no vacancy in the regions 120a and 120b and one or more sample tubes T that were not transferred are held in this sample rack L, this sample rack L is sent out to the relay unit 23, and then, transported, as appropriate, to the measurement units 41, 42, and the smear preparing apparatus 63, in accordance with the transportation destinations of the one or more sample tubes T. Further, in a case where only sample tube(s) T that were not transferred because there was no vacancy in the sorting rack R2 and the archive racks R1 are held in this sample rack L, this sample rack L is sent out to the relay unit 23, then returned to the feeding unit 21, and then sent out to the transport path 140 of the tube sorter 22, again.

With reference back to FIG. 9, the controller 221 of the tube sorter 22 determines whether the sample rack L at the position P2 is empty (S110). When the sample rack L is not empty (S110: NO), the controller 221 causes this sample rack L to be transported to the position P5 (S114). It should be noted that, in the sample rack L at this time, only sample tube(s) T whose transportation destination is the measurement unit 41 remain, as a result of the sample pick-up operation. Then, if there is no sample rack L at the position P231 of the relay unit 23 and this sample rack L can be sent out to the relay unit 23 (S115: YES), the controller 221 causes this sample rack L to be sent out to the relay unit 23 (S116).

On the other hand, the sample rack L is empty (S110: YES), the controller 221 determines whether the value of the first or second sending-out request flag stored in the memory 221a is 1 (S111). It should be noted that the case where the sample rack L is empty in S110 may occur when: an empty sample rack L has been loaded by the user; or all sample tubes T in the sample rack L have been removed through the sample pick-up operation.

Subsequently, when the value of the first or second sending-out request flag is 1 (S111: YES), the controller 221 causes one or more sample tubes T held in the target region of the buffer rack 120 to be transferred to the empty sample rack L located at the position P2 (S112), and sets the value of the target sending-out request flag to 0 (S113).

Specifically, when the value of the first sending-out request flag is 1, one or more sample tubes T held in the region 120a of the buffer rack 120 are transferred to this empty sample rack L. At this time, if the number of the sample tubes T present in the region 120a is 10 or less, all of them are transferred to the empty sample rack L. Then the value of the first sending-out request flag is set to 0. If the number of the sample tubes T present in the region 120a is greater than 10, ten sample tubes T are transferred to the empty sample rack L, in the order of the sample tubes T loaded in the region 120a. When the value of the second sending-out request flag is 1, one or more sample tubes T in the region 120b of the buffer rack 120 are transferred to the empty sample rack L. Also in this case, if the number of the sample tubes T present in the region 120b is 10 or less, all of them are transferred to the empty sample rack L. And the value of the second sending-out request flag is set to 0. If the number of the sample tubes T present in the region 120b is greater than 10, ten sample tubes T are transferred to the sample rack L in the order of the sample tubes T loaded in the region 120b.

If the values of both of the first and second sending-out request flags are 1 at the determination of S111, only one of the processes (e.g., the process regarding the first sending-out request flag) is performed.

In this manner, one or more sample tubes T whose transportation destination is the measurement unit 42 or the smear preparing apparatus 63 are set in the empty sample rack L at the position P2, and this sample rack L is sent out to the relay unit 23 (S114 to S116) in a similar manner with the case where it has been determined as NO in S110.

When the values of the first and second sending-out request flags are both 0 (S111: NO), the controller 221 determines whether the empty rack stocker 110 is full (S117). Specifically, based on a detection signal from the sensor S4, if there is a sample rack L at the position P4, it is determined that the empty rack stocker 110 is full, and if there is no sample rack L at the position P4, it is determined that the empty rack stocker 110 is not full. When the empty rack stocker 110 is full (S117: YES), this sample rack L is sent out to the relay unit 23 as in the case described above (S114 to S116). On the other hand, when the empty rack stocker 110 is not full (S117: NO), the controller 221 causes the rack pushing-out mechanism 151 to push out this sample rack L to the position P3 (S118), whereby this sample rack L is stocked in the empty rack stocker 110.

Thus, the transport process for the sample rack L sent out from the feeding unit 21 to the tube sorter 22 ends.

FIG. 12A is a flow chart of a transport process for a sample rack L stocked in the empty rack stocker 110. This process is started when at least one sample rack L is stocked in the empty rack stocker 110, and is performed in parallel with the transport process shown in FIG. 9.

The controller 221 of the tube sorter 22 determines whether the value of the first or second sending-out request flag stored in the memory 221a is 1 (S301). When the value of the first or second sending-out request flag is 1 (S301: YES), the controller 221 determines whether there is a sample rack L at the position P2 (S302). When it has been determined as NO in S301 or YES in S302, the processing is returned to S301. When it has been determined as YES in S301 and NO in S302, the controller 221 causes an empty sample rack L at the position P3 to be transported to the position P2 (S303).

Subsequently, as in S112 to S116 in FIG. 9, the controller 221 performs processes of S304 to S308 (the part surrounded by broken lines in FIG. 12A). That is, one or more sample tubes T held in the target region of the buffer rack 120 are transferred to the empty sample rack L located at the position P2 (S304), and the value of the target sending-out request flag is set to 0 (S305). Then, this sample rack L is sent out to the relay unit 23 (S306 to S308).

Thus, the transport process for a sample rack L stocked in the empty rack stocker 110 ends.

FIG. 12B is a flow chart showing a process for updating the value of the first sending-out request flag. This process is performed in parallel with the transport processes shown in FIG. 9 and FIG. 12A.

The controller 221 of the tube sorter 22 determines whether the number of sample tubes T in the region 120a of the buffer rack 120 is greater than or equal to a predetermined number (e.g., 10) (S401). When the number of sample tubes T in the region 120a of the buffer rack 120 is less than the predetermined number (S401: NO), the controller 221 determines whether a predetermined time period (e.g., 5 minutes) has elapsed since the latest sample tube T was loaded in the region 120a of the buffer rack 120 (S402). When it has been determined as YES in S401 or S402, the controller 221 sets the value of the first sending-out request flag to 1 (S403). Then, the processing is returned to S401. Also when it has been determined as NO in S402, the processing is returned to S401.

In a case where lapse of time is determined as in S402, the elapsed time period is initialized every time a sample tube T is loaded in the region 120a. Therefore, compared with a case where it is determined whether a predetermined time period has elapsed since a sample tube T was loaded in the region 120a for the first time, the frequency of sample tubes T held in the region 120a to be transferred into an empty sample rack L is reduced. Accordingly, empty sample racks L are less likely to be consumed, and thus, empty sample racks L are more likely to be stocked in the empty rack stocker 110.

A process for updating the value of the second sending-out request flag is also performed in substantially the same manner as that in FIG. 12B. That is, the controller 221 determines whether the number of sample tubes T in the region 120b of the buffer rack 120 is greater than or equal to a predetermined number, and determines whether a predetermined time period has elapsed since the latest sample tube T was loaded in the region 120b of the buffer rack 120. When these determinations are YES, the controller 221 sets the value of the second sending-out request flag to 1.

By always monitoring the state of the sample tubes T in the buffer rack 120 in this manner, the first and second sending-out request flags are updated, the flags indicating whether sample tubes T in the regions 120a and 120b need to be sent out toward the measurement unit 42 and the smear preparing apparatus 63, respectively.

Figure 13A:
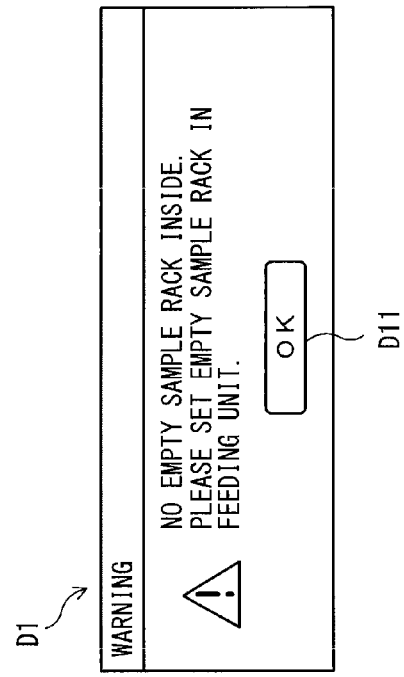
FIG. 13A shows a flow chart showing a process performed when the number of sample racks in the empty rack stocker has become less than a predetermined number according to an embodiment.

FIG. 13A is a flow chart showing a process performed when the number of sample racks L in the empty rack stocker 110 has become less than a predetermined number.

The controller 221 of the tube sorter 22 determines whether the number of empty sample racks L stocked in the empty rack stocker 110 has become less than 1 (S501). When the number of empty sample racks L has become less than 1 (S501: YES), the controller 221 causes the display input section 22a to display a dialogue D1 shown in FIG. 13B. In default state, an OK button D11 of the dialogue D1 is inactive, and the user cannot press it. Until a sample rack L is located at the position P3, the processing is caused to wait (S503).

When the user places an empty sample rack L at the position P211 of the feeding unit 21, this sample rack L is sent out from the feeding unit 21 to the tube sorter 22. Then, this sample rack L is pushed out to the empty rack stocker 110, in accordance with the transport process shown in FIG. 9. That is, after the processes of S101 to S105 in FIG. 9, it is determined as NO in S106, YES in S110, NO in S111, and NO in S117, and then, in S118, the fed empty sample rack L is pushed out into the empty rack stocker 110. As a result, it is detected that the empty sample rack L has been located at the position P3 (S503: YES), and the controller 221 makes the OK button D11 active (S504). When the OK button D11 is pressed by the user (S505: YES), the controller 221 closes the dialogue D1 (S506) and the processing is returned to S501.

As described above, according to the present embodiment, in a case where the sample rack L at the position P2 is empty, if neither the value of the first sending-out request flag nor the value of the second sending-out request flag is 1, such empty sample racks L are transported to the empty rack stocker 110, until the empty rack stocker 110 becomes full. Accordingly, the user need not perform operations such as opening the lid provided to the tube sorter 22 and directly setting an empty sample rack L in the empty rack stocker 110. Therefore, it is possible to alleviate the burden on the user of setting an empty sample rack L.

Further, according to the present embodiment, in a case where all the one or more sample tubes T have been transferred from the sample rack L located at the position P2 and this sample rack L has become empty, if the value of the first or second sending-out request flag is 1, one or more target sample tubes T are transferred to this sample rack L. Accordingly, compared with a case where an empty sample rack L in the empty rack stocker 110 is transported to the position P2, it is possible to quickly transfer the target sample tubes T.

Further, according to the present embodiment, among the sample tubes T held in a sample rack L located at the position P2, sample tubes T to be transported to the measurement unit 41 and the smear preparing apparatus 63 are transferred to the regions 120a and 120b, respectively. Then, one or more sample tubes T held in the region 120a are transferred to a sample rack L supplied from the empty rack stocker 110, and one or more sample tubes T held in the region 120b are transferred into a sample rack L supplied from the empty rack stocker 110. Since transfer of a sample tube T is performed in accordance with its transportation destination based on its test type in this manner, it is possible to transport a sample rack L having collected therein a plurality of sample tubes T that have the same transportation destination, to that transportation destination, and thus, sample processing can be performed effectively.

Further, according to the present embodiment, the empty rack stocker 110 is provided so as to be connected to the transport path 140, at the position P2 of the transport path 140, with a width greater than the width in the longitudinal direction of a sample rack L. A sample rack L at the position P2 is pushed out, by the rack pushing-out mechanism 151, in the direction that crosses the transport direction of the transport path 140, to be located at the position P3 which is in a front portion of the empty rack stocker 110. Accordingly, a sample rack L that has become empty can be quickly transported from the transport path 140 to the empty rack stocker 110, and thus, stagnation of the sample rack L can be suppressed.

Further, according to the present embodiment, the storage region 112 of the empty rack stocker 110 is provided so as to extend in the direction (front-rear direction) perpendicular to the direction (left-right direction) in which the transport path 140 extends at the position P2. Accordingly, it is possible to stock an empty sample rack L in the empty rack stocker 110, simply by moving the empty sample rack L from the transport path 140 to the empty rack stocker 110. In addition, the mechanism and control for stocking an empty sample rack L is simplified.

Figure 13B:
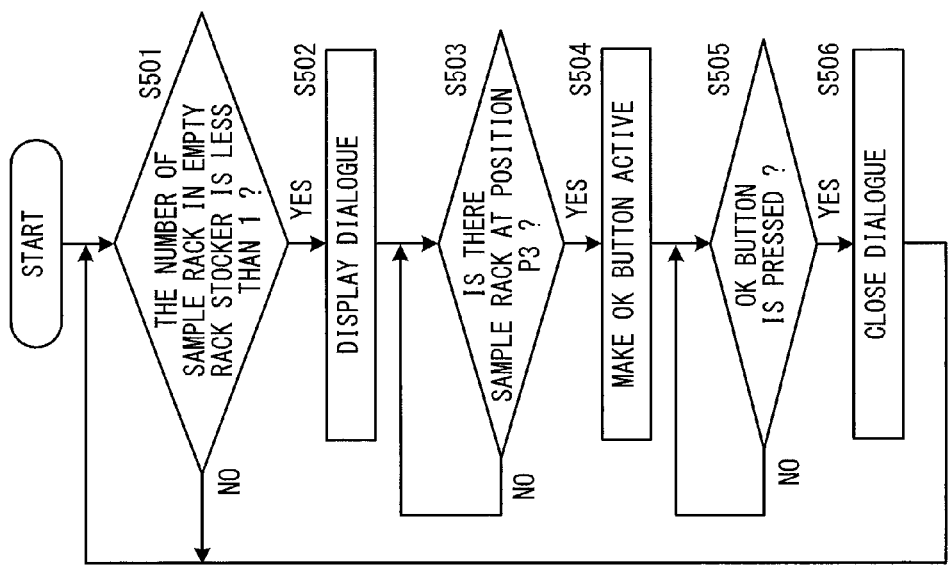
FIG. 13B shows a dialogue displayed in a display input section, according to an embodiment.

Further, according to the present embodiment, when the number of sample racks L stocked in the empty rack stocker 110 is less than 1, the dialogue D1 shown in FIG. 13B is displayed in the display input section 22a. This allows the user to notice shortage of sample racks L stocked in the empty rack stocker 110, and thus, the user can take measures such as placing an empty sample rack L in the feeding unit 21. Therefore, it is possible to suppress the sample transfer operation from being abruptly suspended, due to shortage of empty sample racks L.

Further, according to the present embodiment, when sample tube(s) T held in the region 120a or 120b of the buffer rack 120 are transferred to a sample rack L transported from the empty rack stocker 110 to the position P2, this sample rack L is sent out to the relay unit 23 along the transport path 140. Accordingly, the transferred sample tube(s) T can be transported to a corresponding one of the measurement unit 42 and the smear preparing apparatus 63, not via the hands of the user.

Further, according to the present embodiment, after the processing by the measurement units 41 and 42 and the smear preparing apparatus 63 has been completed, sample tube(s) T that do not need re-processing are transferred to holder(s) R11 in the archive racks R1, and only sample tube(s) T that need processing are held in a sample rack L. Accordingly, even in a case where a sample rack L located at the position P2 includes sample tube(s) T that need processing and sample tube(s) T for which processing has been completed, it is possible to transport the sample rack L holding only the sample tube(s) T that need processing, to the measurement units 41, 42 or the smear preparing apparatus 63.

Further, according to the present embodiment, a sample rack L that holds sample tube(s) T for which processing by the measurement unit 41, 42 or the smear preparing apparatus 63 has been completed, and that has been sent out from the relay unit 23 to the transport path 160 of the tube sorter 22, is sent out to the feeding unit 21 along the transport path 160. The feeding unit 21 is configured to be able to send out a sample rack L sent out from the tube sorter 22, to the transport path 140 of the tube sorter 22 again. Since the sample rack L holding sample tube(s) T for which processing has been completed can be supplied, via the transport path 160, again to the transport path 140, it is possible to transport, not via the hands of the user, sample tube(s) T which need re-processing in the measurement unit 41, 42, or the smear preparing apparatus 63, to the measurement unit 41, 42, or the smear preparing apparatus 63.

Further, according to the present embodiment, when an empty sample rack L is placed in the feeding unit 21, this sample rack L is sent out to the transport path 140 of the tube sorter 22. Then, if neither the value of the first sending-out request flag nor the value of the second sending-out request flags is 1, and the empty rack stocker 110 is not full, this sample rack L is pushed out into the empty rack stocker 110, by the rack pushing-out mechanism 151. Accordingly, it is possible to supplement the empty rack stocker 110 with an empty sample rack L, while alleviating the burden on the user.

An embodiment of the present invention has been described. However, the embodiment of the present invention is not limited thereto.

For example, the above embodiment has shown an example in which blood is measured in the measurement units 41 and 42. However, urine may be measured by the measurement units 41 and 42. That is, the present invention can be applied to a sample processing system that includes measurement units for measuring urine. Further, the present invention can be applied to a clinical sample processing system that includes measurement units for measuring other clinical samples.

Further, in the above embodiment, the empty rack stocker 110 is provided adjacent to the position P2 at which transfer of a sample tube T is performed. However, the present invention is not limited thereto. The empty rack stocker 110 may be provided, distanced from the position P2 in a direction (left-right direction) along the transport path 140. In this case, an empty sample rack L, from which its one or more sample tubes T have been all unloaded at the position P2, is transported along the transport path 140 to a front position facing the empty rack stocker 110, and then, this sample rack L is pushed out by the rack pushing-out mechanism 151 into the empty rack stocker 110.

Further, in the above embodiment, as shown in FIG. 9, with a sample rack L located at the position P2, the sample pick-up operation is performed and one or more sample tubes T are transferred from the buffer rack 120. However, the present invention is not limited thereto. With a sample rack L located at the position P3, a transfer operation for a sample tube T may be performed. The transport process for a sample rack L in this case will be described with reference to FIGS. 14 and 15A.

Figure 14:
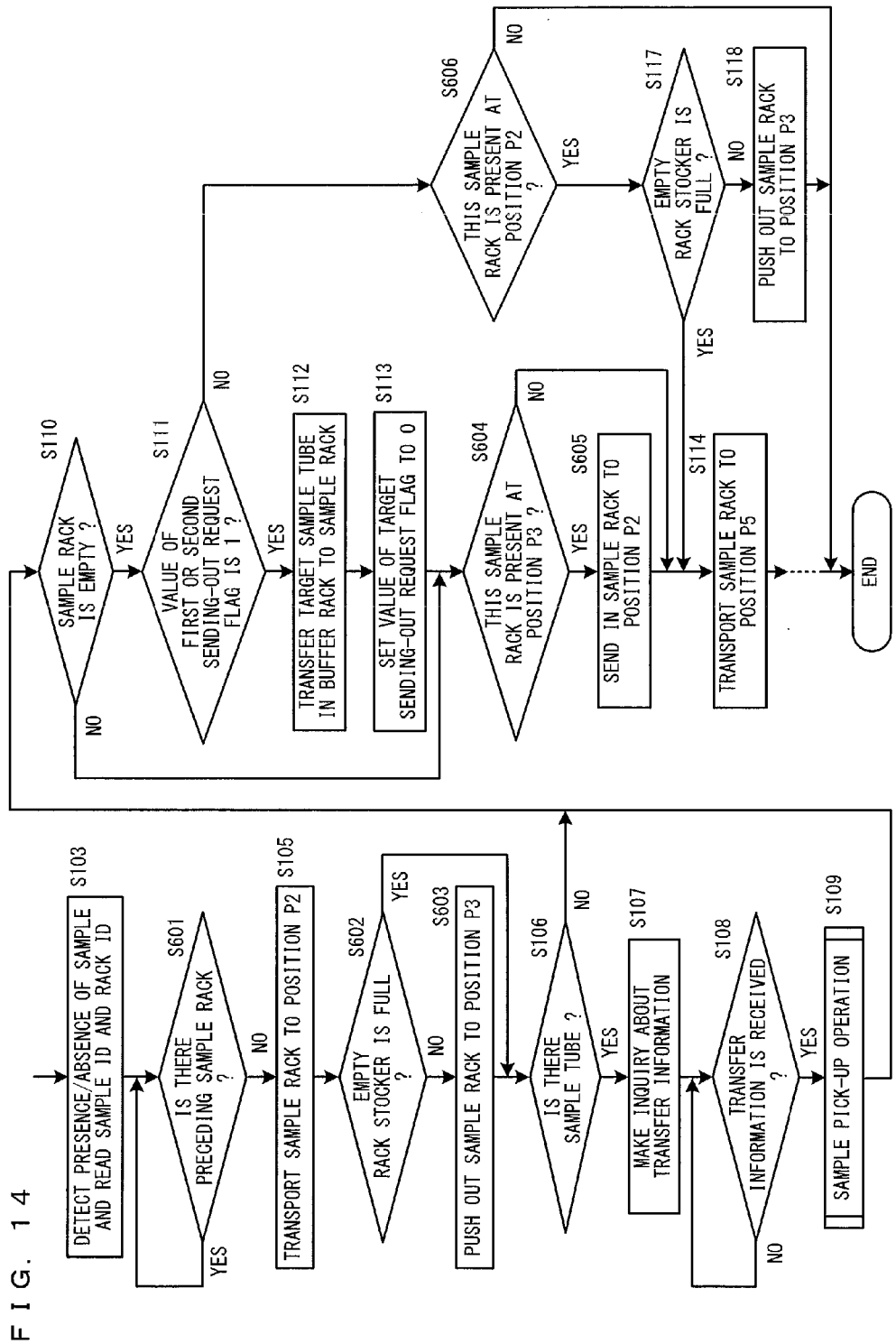
FIG. 14 is a flow chart showing a transport process for a sample rack sent out from a feeding unit to a tube sorter according to a modification.

FIG. 14 is a flow chart showing a transport process for a sample rack L sent out from the feeding unit 21 to the tube sorter 22. The transport process shown in FIG. 14 is equivalent to the transport process shown in FIG. 9, from which S104 and S107 are omitted, and to which S601 to S606 are added. S101, S115, and S116 are not shown for convenience.

Upon completion of detection and reading by the bar code unit B (S103), the controller 221 causes the processing to wait until transportation of the preceding sample rack L is completed by the transport process shown in FIG. 14 (S601). After the transportation of the preceding sample rack L is completed (S601: NO), and when a sample rack L is located at the position P2 (S105), if the empty rack stocker 110 is not full (S602: NO), the controller 221 causes this sample rack L to be pushed out to the position P3 (S603), and if the empty rack stocker 110 is full (S602: YES), the controller 221 advances the processing to S106.

When having determined in S106 that one or more sample tubes T are present in the sample rack L (S106: YES), then, in S107 and S108, the controller 221 obtains transfer information, and based on the obtained transfer information, the controller 221 causes the sample pick-up operation to be performed (S109). In the process flow shown in FIG. 14, at the execution of the sample pick-up operation, the sample rack L is located at either of the position P2 (S105) or the position P3 (S603). In accordance with which of the positions P2 and P3 the sample rack L is located, the controller 221 changes the position for picking up a sample tube T in the tube conveyor 130.

When having determined that there is no sample rack L in the sample tube T in S106 (S106: NO), the controller 221 advances the processing to S110.

Next, in S110, the controller 221 determines whether one or more sample tubes T are held in the sample rack L at the position P2 or the position P3. It should be noted that the one or more sample tube T held in the sample rack L are sample tubes T that were not transferred by the sample pick-up operation in step S109 and whose transportation destination is the measurement unit 41. When one or more sample tubes T are held in the sample rack L (S110: NO), then, in S604, the controller 221 determines at which of the position P3 and the position P2 this sample rack L is present. When the sample rack L is present at the position P3 (S604: YES), the controller 221 causes the sample rack L to be sent to the position P2 (S605), and then, causes the sample rack L to be transported to the position P5 (S114). On the other hand, when the sample rack L is present at the position P2 (S604: NO), the controller 221 causes the sample rack L to be transported to the position P5 (S114).

When no sample tube T is held in the sample rack L in the determination in S110 (S110: YES), if either one of the values of the first sending-out request flag and the second sending-out request flag is 1 (S111: YES), the controller 221 performs the processes of S112 and 113, to transfer one or more sample tubes T in the target region of the buffer rack 120 into the sample rack L. Thereafter, the controller 211 performs the processes of S604 and thereafter, to transport the sample rack L to the position P5.

When neither the value of the first sending-out request flag nor the value of the second sending-out request flag is 1 (S111: NO), then, in S606, the controller 221 determines at which of the position P3 and the position P2 this sample rack L is present. When the sample rack L is present at the position P3 (S606: NO), the controller 221 ends the process. On the other hand, when the sample rack L is present at the position P2 (S606: YES), the controller 221 determines whether the empty rack stocker 110 is full (S117). When the empty rack stocker 110 is not full (S117: NO), the controller 221 causes the sample rack L to be pushed out to the position P3, thereby stocking the sample rack L in the empty rack stocker 110 (S118), and ends the process. When the empty rack stocker 110 is full (S117: YES), the controller 221 causes the sample rack L to be transported to the position P5 (S114). The processes of S114 and thereafter are the same as those in FIG. 9.

Figure 15A:
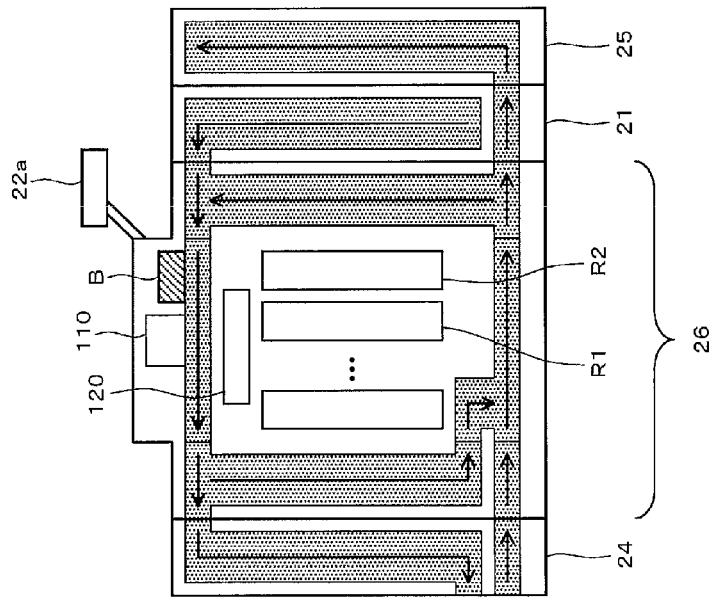
FIG. 15A shows a flow chart showing a transport process for a sample rack stocked in an empty rack stocker according to a modification.

FIG. 15A is a flow chart showing a transport process for a sample rack L stocked in the empty rack stocker 110. The transport process shown in FIG. 15A is equivalent to the transport process shown in FIG. 12A, from which S302 and S303 are omitted, and to which S701 and S702 are added. Hereinafter, the difference of the transport process in FIG. 15A from that in FIG. 12A will be described.

In S304, to an empty sample rack L located at the position P3, one or more sample tubes T in the target region are transferred. In S701, it is determined whether a sample rack L is present at the position P2. When there is no sample rack L at the position P2 (S701: NO), the controller 221 causes the sample rack L located at the position P3 to be sent to the position P2 (S702).

Also in the modification shown in FIG. 14 and FIG. 15A, as in the above embodiment, the effect of alleviating the burden on the user of setting an empty sample rack L can be exhibited. However, in the above embodiment, there is no need to switch the position for transferring a sample tube T between the position P2 and the position P3. Thus, the above embodiment is preferred because control of the belt 141, the rack pushing-out mechanism 151, and the tube conveyor 130 is simplified.

In the above embodiment, when the number of sample racks L in the empty rack stocker 110 becomes less than 1, the dialogue D1 is displayed in the display input section 22a. However, the present invention is not limited thereto. The controller 221 may cause a sound to be emitted from a speaker installed in the tube sorter 22. Alternatively, information of the number of sample racks L being less than 1 may be transmitted to the host computer 8 via the transport controller 7, and information of the number of sample racks L in the empty rack stocker 110 being less than 1 may be displayed in the display section on the host computer 8 side. "Outputs a predetermined notification" described in claims includes outputting information for giving notification to another apparatus such as the host computer 8 as described above.

Further, the dialogue D1 may be displayed when the number of sample racks L in the empty rack stocker 110 has become less than a value other than 1. In this case, the display of the dialogue D1 is changed to, for example, "There are few empty sample racks stocked inside. Please set an empty sample rack in the feeding unit." In this case, in order to detect that the number of sample racks L in the empty rack stocker 110 has become less than a value other than 1, a sensor is installed in the empty rack stocker 110 as appropriate.

Figure 15B:
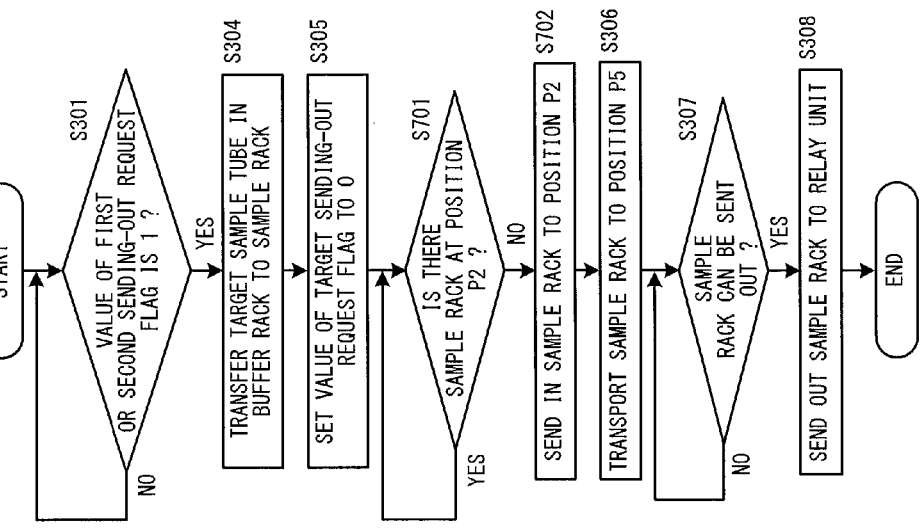
FIG. 15B shows a structure of a tube sorter according to a modification, viewed from above.

Further, in the above embodiment, an empty sample rack L that has been sent out from the tube sorter 22 to the relay unit 23 and holds no sample tube T is returned to the tube sorter 22 again by the relay unit 23. Moreover, a sample rack L that has been sent out from the tube sorter 22 to the feeding unit 21 and holds one or more sample tubes T is returned to the tube sorter 22 again by the feeding unit 21. However, as shown in a tube sorter 26 shown in FIG. 15B, the tube sorter may be configured such that the feeding unit 21, the tube sorter 22, and the relay unit 23 of the above embodiment are integrated.

Further, in the above embodiment, one or more sample tubes T unloaded from a sample rack L sent into the transport path 140 are conveyed to the buffer rack 120, and one or more sample tubes T unloaded from the buffer rack 120 are transferred, in accordance with the transportation destination thereof, to another sample rack L supplied from the empty rack stocker 110. However, the present invention is not limited thereto. One or more sample tubes T unloaded from the sample rack L sent into the transport path 140 may be transferred to another sample rack L supplied from the empty rack stocker 110, not via the buffer rack 120. For example, in a case where a sample rack L sent into the transport path 140 includes sample tubes T whose transportation destinations are different, sample tubes T unloaded from the sample rack L may be allocated to a plurality of sample racks L in the empty rack stocker 110, in accordance with their transportation destinations, not via the buffer rack 120. For example, in a case where each of two successive sample racks L sent into the transport path 140 includes sample tubes T whose transportation destination is the measurement unit 41, sample tubes T whose transportation destination is the measurement unit 42, and sample tubes T whose transportation destination is the smear preparing apparatus 63, sample tubes T unloaded from the two sample racks L located on the feeding unit 21 side relative to the position P2 of the transport path 140 may be allocated to three sample racks L in the empty rack stocker 110, in accordance with their transportation destinations. In this case, a sample rack L housing only sample tubes T whose transportation destination is the measurement unit 41, a sample rack L housing only sample tubes T whose transportation destination is the measurement unit 42, and a sample rack L housing only sample tubes T whose transportation destination is the smear preparing apparatus 63 are supplied from the empty rack stocker 110 to the transport path 140, and these sample racks L are transported toward their respective transportation destinations. Thereafter, the two sample racks L which have become empty and which are on the transport path 140 may be conveyed to the empty rack stocker 110. Still alternatively, the following configuration may be employed. A plurality of conveying paths connected to the relay unit 23 are provided separately from the transport path 140, and a rack supplier (such as rack gripper) which supplies a sample rack L in the empty rack stocker 110 into each conveying path is provided. Then, each sample tube T unloaded from a sample rack L sent into the transport path 140 is transferred, not via the buffer rack 120, into the sample rack L on a corresponding one of the conveying paths in accordance with the transportation destination of the sample tube T, and then, the sample rack L which has become empty and which is on the transport path 140 is conveyed to the empty rack stocker 110.

Further, in the above embodiment, both of the sample rack L sent in from the feeding unit 21 and the sample rack L supplied from the empty rack stocker 110 are transported by the transport path 140 provided to the front of the empty rack stocker 110. However, the present invention is not limited thereto. For example, another transport path connected to the relay unit 23 may be provided also to the rear of the empty rack stocker 110, separately from the transport path 140. Then, the sample rack L sent in from the feeding unit 21 is transported by the transport path 140 and a sample rack L stocked in the empty rack stocker 110 may be transported to the relay unit 23 by the transport path provided to the rear of the empty rack stocker 110.

Further, in the above embodiment, the two measurement unit 41 and 42 and one smear preparing apparatus 63 are arranged on the downstream side of the tube sorter 22. However, the type, the number, and the arrangement positions of sample processing apparatuses connected to the tube sorter 22 are not limited thereto. For example, the number of measurement units arranged may be one, or three or more. Presence/absence or the number of smear preparing apparatus may also be changed. Still further, a blood sedimentation measurement apparatus may be added, and the sample processing apparatuses may be arranged on the upstream side.

In addition to the above, various modifications of the embodiment of the present invention may be made as appropriate, without departing from the scope of the technical idea defined by the claims.

What is claimed is:

1. A tube sorter comprising:
a controller coupled to a memory that stores operational programs executable by the controller;
a rack stocker configured to stock therein a plurality of empty sample racks, each empty sample rack capable of holding one or more sample tubes, the rack stocker including a storage region configured to sequentially store the one or more empty sample racks therein;
a transporting section coupled to the controller, the controller configured to command the transporting section to transport sample racks along a transport path, the storage region sequentially storing the one or more empty sample racks in a direction perpendicular to a direction of the transport path;
an archive rack configured to store a plurality of sample tubes;
a buffer rack configured to temporarily store a plurality of sample tubes;
a tube conveyor including a guide arranged above the transporting section and the rack stocker, a sliding part slidably coupled to the guide and having an ascending/descending part with a gripper attached thereto, the controller configured to command the tube conveyor to perform:
a first operation of loading sample tubes held by a sample rack transported to the transport path by the transporting section to the archive rack or the buffer rack, or both, by gripping and vertically moving and horizontally moving each of the sample tubes and
a second operation of loading one or more sample tubes stored in the buffer rack to an empty rack at a predetermined position and not holding sample tubes by gripping and vertically moving and horizontally moving each sample tube;
a rack pushing mechanism configured to convey an empty sample rack to the rack stocker by pushing the empty sample rack at the predetermined position onto the rack stocker; and
a rack sending mechanism opposite the transport path from the rack pushing mechanism and configured to convey the empty sample rack from the rack stocker to the predetermined position for action by the second operation of the tube conveyor,
wherein the controller commands the transporting section to transfer a loaded sample rack which holds sample tubes and is provided for the first operation of the tube conveyor at the predetermined position along transport path, and the controller commands the rack pushing mechanism to convey the unloaded sample rack, after being emptied by performing the first operation, to the rack stocker.

2. The tube sorter according to claim 1, wherein the controller commands the tube conveyor to perform the first operation by loading all of the sample tubes held by the sample rack to the archive rack and/or the buffer rack.

3. The tube sorter according to claim 1, wherein the controller commands the rack sending mechanism to convey one of the plurality of empty sample racks from the rack stocker to the predetermined position on the transport path, and
the tube conveyor loads one or more sample tubes stored in the buffer rack onto the one empty sample rack.

4. The tube sorter according to claim 1, wherein the controller is coupled to a sensor that resides in proximity to the storage region and is configured to detect whether the storage region is full by the empty sample racks, and in response to detecting that the storage region is full, the controller commands the tube conveyor to perform the second operation by loading the one or more sample tubes stored in the buffer rack onto the loaded sample rack emptied by performing the first operation.

5. The tube sorter according to claim 1, wherein the controller commands the tube conveyor to unload each of the sample tubes from the loaded sample rack at the predetermined position and to store a selected sample tube among the unloaded sample tubes in the buffer rack.

6. The tube sorter according to claim 1, wherein the rack pushing mechanism is configured to push out the empty sample rack located at the predetermined position in the transport path, into a direction that crosses the transport path, and the rack stocker is arranged at a position to receive the empty sample rack pushed out from the predetermined position.

7. The tube sorter according to claim 1, wherein the controller is coupled to a sensor that resides in proximity to the storage region and is configured to sense the presence of the empty sample racks, wherein when the number of empty sample racks remaining in the rack stocker, as determined by input from the sensors, is less than a predetermined number, the controller outputs a notification to a display.

8. The tube sorter according to claim 1, further comprising a feeding unit capable of receiving a new loaded sample rack holding one or more sample tubes from a user, and wherein the controller commands the transporting section to transport the new loaded sample rack received from the feeding unit to the predetermined position, and the controller commands the tube conveyor to perform the first operation with the new loaded sample rack.

9. The tube sorter according to claim 1, wherein the transporting section is connected by a relay unit to a sample processing apparatus configured to process a sample in a sample tube, and the controller commands the transporting section to send out a loaded sample rack on which a sample tube has been loaded by the second operation of the tube conveyor, to the relay unit for transferring to the sample processing apparatus.

10. The tube sorter according to claim 8, wherein
the archive rack is configured to house the one or more sample tubes that do not need to be processed,
the buffer rack is configured to house the one or more sample tubes that do need to be processed, and
the sample tubes held by the sample rack comprises a first sample tube and a second sample tube, wherein
the controller commands the tube conveyor to
(a) unload the first sample tube from the sample rack and loads the first sample tube to the archive rack, and
(b) unload the second sample tube from the sample rack and loads the second sample tubes to the buffer rack.

11. The tube sorter according to claim 9, wherein the transporting section further comprises a feeding unit configured to receive a new loaded sample rack holding sample tubes and to supply the new loaded sample rack to the transporting section.

12. The tube sorter according to claim 1, further comprising:
an identification information obtainer configured to obtain identification information of sample tubes held in the loaded sample rack,
wherein based on the identification information obtained from the one or more sample tubes on the loaded sample rack, the controller commands the tube conveyor to load the one or more sample tubes to the archive rack and/or the buffer rack.

13. The tube sorter according to claim 12, wherein the controller relays the identification information to a host computer, that stores measurement orders for each of the one or more sample tubes, and receives transfer information from the host computer, and the controller selects, from among the one or more sample tubes held by the loaded sample rack, a sample tube to be loaded to the buffer rack based on transfer information, and commands the tube conveyor to load the selected sample tube to the buffer rack.

14. The tube sorter according to claim 1, further comprising:
a feeding unit configured to receive a new loaded sample rack holding sample tubes from a user and to supply the new loaded sample rack to the transport path,
wherein the transporting section includes a second transport path which is connected to the feeding unit and is configured to transport the new loaded sample rack to direction opposite to the transport path, and
the feeding unit is configured to receive the new loaded sample rack from the second transport path and to transport the new loaded sample rack to the transport path.

15. A sample processing system comprising:
the tube sorter according to claim 1, and
a sample processing apparatus connected to a relay unit and configured to process a sample in a sample tube, wherein
the relay unit is configured to receive the loaded sample rack holding sample tubes loaded by the second operation from the tube sorter and to transport the loaded sample rack to the sample processing apparatus.

16. The sample processing system according to claim 15, further comprising:
a feeding unit configured to receive a new loaded sample rack from a user and to supply the new loaded sample rack to the tube sorter.

17. A tube sorter comprising:
a controller coupled to a memory that stores operational programs executable by the controller;
a transporting section coupled to the controller, and the controller configured command the transport section to transport sample racks along a transport path;
a rack stocker configured to stock therein one or more empty sample racks and arranged adjacent to the transport path;
an archive rack configured to store a plurality of sample tubes;
a buffer rack configured to temporarily store a plurality of sample tubes;
a tube conveyor including a guide arranged above the transporting section and the rack stocker, a sliding part slidably coupled to the guide and having an ascending/descending part with a gripper attached thereto, the controller configured to command the tube conveyor to perform a first operation of transferring sample tubes held by a sample rack to the archive rack and/or the buffer rack and a second operation of transferring sample tubes stored in the buffer rack to an empty rack not holding sample tubes;
a rack pushing mechanism configured to convey an empty sample rack to the rack stocker by pushing the empty sample rack positioned at a predetermined position on the transport path; and
a rack sending mechanism configured to convey one of the empty sample racks stocked in the rack stocker to the predetermined position on the transport path for using the second operation of the tube conveyor,
wherein the controller commands the transporting section to transfer a loaded sample rack which holds sample tubes and is provided for the first operation of the tube conveyor at the predetermined position along the transport path, and
the controller commands the rack pushing mechanism to convey the unloaded sample rack at the predetermined position, after being emptied by performing the first operation, to the rack stocker.

18. The tube sorter according to claim 17, wherein the controller commands the tube conveyor to perform the first operation by transferring all of the sample tubes held by the loaded sample rack at the predetermined position to the archive rack and/or the buffer rack, and the controller commands the rack pushing mechanism to convey the unloaded sample rack at the predetermined position, after being emptied by performing the first operation of the tube conveyor, to the rack stocker.

19. The tube sorter according to claim 17, wherein the controller commands the rack sending mechanism to convey the empty sample rack from the rack stocker to the transport path, and the tube conveyor loads one or more sample tubes stored in the buffer rack onto the empty sample rack.

20. The tube sorter according to claim 17, when the controller determines that the rack stocker is full, the controller commands the tube conveyor to perform the second operation by loading sample tubes stored in the buffer rack onto the loaded sample rack at the predetermined position emptied by performing the first operation.

21. A sample processing system comprising:

the tube sorter according to claim 14, and a sample processing apparatus connected to a relay unit and configured to process a sample in a sample tube, wherein the relay unit is connected to the transport path and the second transport path, and is configured to transport the new loaded sample rack to the sample processing apparatus, to receive the new loaded sample rack from the sample processing apparatus, and to transport the received sample rack to the second transport path.

* * * * *